United States Patent
Li et al.

(10) Patent No.: US 9,279,767 B2
(45) Date of Patent: *Mar. 8, 2016

(54) CHEMICAL-ANALYSIS DEVICE INTEGRATED WITH METALLIC-NANOFINGER DEVICE FOR CHEMICAL SENSING

(75) Inventors: Zhiyong Li, Redwood City, CA (US); R. Stanley Williams, Portola Valley, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 194 days.

This patent is subject to a terminal disclaimer.

(21) Appl. No.: 13/879,255

(22) PCT Filed: Oct. 20, 2010

(86) PCT No.: PCT/US2010/053343
§ 371 (c)(1),
(2), (4) Date: Apr. 12, 2013

(87) PCT Pub. No.: WO2012/054027
PCT Pub. Date: Apr. 26, 2012

(65) Prior Publication Data
US 2013/0217143 A1    Aug. 22, 2013

(51) Int. Cl.
*G01N 21/00* (2006.01)
*G01N 21/64* (2006.01)
*G01N 21/65* (2006.01)

(52) U.S. Cl.
CPC .......... *G01N 21/6428* (2013.01); *G01N 21/648* (2013.01); *G01N 21/658* (2013.01)

(58) Field of Classification Search
None
See application file for complete search history.

(56) References Cited

U.S. PATENT DOCUMENTS

| | | | |
|---|---|---|---|
| 4,901,231 A | 2/1990 | Bishop et al. | |
| 5,455,953 A | 10/1995 | Russell | |
| 5,513,314 A | 4/1996 | Kandasamy et al. | |

(Continued)

FOREIGN PATENT DOCUMENTS

| | | |
|---|---|---|
| CN | 101688809 | 3/2010 |
| EP | 1426756 | 6/2004 |

(Continued)

OTHER PUBLICATIONS

Hu, Min et al., "Gold Nanofingers for Molecule Trapping and Detection", J. Am. Chem. Soc. 2010, (Aug. 26, 2010) 3 pgs.

(Continued)

*Primary Examiner* — Robert Xu
(74) *Attorney, Agent, or Firm* — HP Inc. Patent Department

(57) ABSTRACT

A chemical-analysis device integrated with a metallic-nanofinger device for chemical sensing. The chemical-analysis device includes a metallic-nanofinger device, and a platform. The metallic-nanofinger device includes a substrate, and a plurality of nanofingers coupled with the substrate. A nanofinger of the plurality includes a flexible column, and a metallic cap coupled to an apex of the flexible column. At least the nanofinger and a second nanofinger of the plurality of nanofingers are to self-arrange into a close-packed configuration with at least one analyte molecule. A morphology of the metallic cap is to generate a shifted plasmonic-resonance peak associated with amplified luminescence from the analyte molecule. A method for using, and a chemical-analysis apparatus including the chemical-analysis device are also provided.

12 Claims, 18 Drawing Sheets

(56) References Cited

U.S. PATENT DOCUMENTS

| | | |
|---|---|---|
| 5,677,196 A | 10/1997 | Herron et al. |
| 5,828,876 A | 10/1998 | Fish et al. |
| 5,873,103 A | 2/1999 | Trede et al. |
| 5,909,540 A | 6/1999 | Carter et al. |
| 5,948,062 A | 9/1999 | Tzelnic et al. |
| 5,960,446 A | 9/1999 | Schmuck et al. |
| 5,987,506 A | 11/1999 | Carter et al. |
| 6,023,706 A | 2/2000 | Schmuck et al. |
| 6,163,801 A | 12/2000 | O'Donnell et al. |
| 6,173,293 B1 | 1/2001 | Thekkath et al. |
| 6,182,111 B1 | 1/2001 | Inohara et al. |
| 6,185,601 B1 | 2/2001 | Wolff |
| 6,192,408 B1 | 2/2001 | Vahalia et al. |
| 6,193,870 B1 | 2/2001 | Morse et al. |
| 6,222,619 B1 | 4/2001 | Herron et al. |
| 6,324,581 B1 | 11/2001 | Xu et al. |
| 6,330,572 B1 | 12/2001 | Sitka |
| 6,345,244 B1 | 2/2002 | Clark |
| 6,356,863 B1 | 3/2002 | Sayle |
| 6,389,420 B1 | 5/2002 | Vahalia et al. |
| 6,442,608 B1 | 8/2002 | Knight et al. |
| 6,453,354 B1 | 9/2002 | Jiang et al. |
| 6,516,320 B1 | 2/2003 | Odom et al. |
| 6,571,259 B1 | 5/2003 | Zheng et al. |
| 6,654,912 B1 | 11/2003 | Viswanathan et al. |
| 6,756,795 B2 | 6/2004 | Hunt et al. |
| 6,772,161 B2 | 8/2004 | Mahalingam et al. |
| 6,777,244 B2 | 8/2004 | Pepper et al. |
| 6,782,389 B1 | 8/2004 | Chrin et al. |
| 6,823,336 B1 | 11/2004 | Srinivasan et al. |
| 6,938,039 B1 | 8/2005 | Bober et al. |
| 6,973,455 B1 | 12/2005 | Vahalia et al. |
| 7,158,219 B2 | 1/2007 | Li et al. |
| 7,236,242 B2 | 6/2007 | Kamins et al. |
| 7,245,370 B2 | 7/2007 | Bratkovski et al. |
| 7,256,886 B2 | 8/2007 | Cullum et al. |
| 7,342,479 B2 | 3/2008 | Glatkowski et al. |
| 7,342,656 B2 | 3/2008 | Islam et al. |
| 7,357,906 B2 | 4/2008 | Colbert et al. |
| 7,388,661 B2 | 6/2008 | Li et al. |
| 7,402,531 B1 | 7/2008 | Kuekes et al. |
| 7,483,130 B2 | 1/2009 | Baumberg et al. |
| 7,528,948 B2 | 5/2009 | Bratkovski et al. |
| 7,583,379 B2 | 9/2009 | Zhao et al. |
| 7,597,814 B2 | 10/2009 | Stasiak et al. |
| 7,656,525 B2 | 2/2010 | Zhao et al. |
| 7,667,238 B2 | 2/2010 | Erchak |
| 7,833,842 B2 | 11/2010 | Williams |
| 7,960,251 B2 | 6/2011 | Choi et al. |
| 8,108,943 B2 | 1/2012 | Anderson |
| 8,148,294 B2 | 4/2012 | Wang et al. |
| 8,149,397 B2 | 4/2012 | Lee et al. |
| 8,154,722 B2 | 4/2012 | Yamada et al. |
| 8,184,284 B2 | 5/2012 | Ebstein |
| 8,279,435 B2 | 10/2012 | Wang et al. |
| 2002/0059309 A1 | 5/2002 | Loy et al. |
| 2002/0095479 A1 | 7/2002 | Schmidt |
| 2002/0120763 A1 | 8/2002 | Miloushev et al. |
| 2002/0138501 A1 | 9/2002 | Dake |
| 2002/0138502 A1 | 9/2002 | Gupta |
| 2002/0143734 A1 | 10/2002 | Loy et al. |
| 2002/0161855 A1 | 10/2002 | Manczak et al. |
| 2002/0192721 A1 | 12/2002 | Rizzuto et al. |
| 2003/0004947 A1 | 1/2003 | Coverston |
| 2003/0028587 A1 | 2/2003 | Driscoll et al. |
| 2003/0033308 A1 | 2/2003 | Patel et al. |
| 2003/0077023 A1 | 4/2003 | Troll |
| 2003/0079222 A1 | 4/2003 | Boykin et al. |
| 2003/0110237 A1 | 6/2003 | Kitamura et al. |
| 2003/0115434 A1 | 6/2003 | Mahalingam et al. |
| 2003/0115438 A1 | 6/2003 | Mahalingam et al. |
| 2004/0106203 A1 | 6/2004 | Stasiak et al. |
| 2004/0133570 A1 | 7/2004 | Soltis |
| 2006/0119853 A1 | 6/2006 | Baumberg |
| 2006/0213259 A1 | 9/2006 | Prinz et al. |
| 2006/0231381 A1 | 10/2006 | Jensen |
| 2006/0252065 A1 | 11/2006 | Zhao et al. |
| 2007/0020445 A1 | 1/2007 | Liu et al. |
| 2007/0070341 A1 | 3/2007 | Wang et al. |
| 2007/0086001 A1 | 4/2007 | Islam et al. |
| 2007/0127164 A1 | 6/2007 | Ofek |
| 2007/0132043 A1 | 6/2007 | Bradley et al. |
| 2007/0252982 A1 | 11/2007 | Wang |
| 2008/0017845 A1 | 1/2008 | Drndic |
| 2008/0024776 A1 | 1/2008 | Bratkovski et al. |
| 2008/0094621 A1 | 4/2008 | Li |
| 2008/0144026 A1 | 6/2008 | Zhao et al. |
| 2008/0174775 A1 | 7/2008 | Moskovits et al. |
| 2008/0187648 A1 | 8/2008 | Hart |
| 2008/0311028 A1 | 12/2008 | Stanbery |
| 2009/0084162 A1 | 4/2009 | Besnard et al. |
| 2009/0227059 A1 | 9/2009 | Besnard et al. |
| 2009/0261815 A1 | 10/2009 | Cairns |
| 2009/0280593 A1 | 11/2009 | Serban et al. |
| 2009/0303472 A1 | 12/2009 | Zhao et al. |
| 2009/0317943 A1 | 12/2009 | Park et al. |
| 2010/0001211 A1 | 1/2010 | Juang et al. |
| 2010/0009338 A1 | 1/2010 | Zhang et al. |
| 2010/0303722 A1 | 12/2010 | Jin et al. |
| 2010/0321684 A1 | 12/2010 | Bratkovski et al. |
| 2011/0001118 A1 | 1/2011 | Bhupendra |
| 2011/0030792 A1 | 2/2011 | Miguez |
| 2011/0128537 A1 | 6/2011 | Bond et al. |
| 2011/0188034 A1 | 8/2011 | Stuke et al. |
| 2012/0107948 A1 | 5/2012 | Li et al. |
| 2012/0119315 A1 | 5/2012 | Ou et al. |
| 2012/0188540 A1 | 7/2012 | Bratkovski et al. |
| 2012/0212732 A1 | 8/2012 | Santori et al. |
| 2012/0212733 A1 | 8/2012 | Kodali et al. |
| 2013/0027698 A1 | 1/2013 | Li et al. |
| 2013/0120748 A1 | 5/2013 | Li et al. |

FOREIGN PATENT DOCUMENTS

| | | |
|---|---|---|
| EP | 2058908 | 5/2009 |
| JP | 2000206048 | 7/2000 |
| JP | 2004184414 | 2/2004 |
| JP | 2009515543 | 4/2009 |
| JP | 2009544967 | 12/2009 |
| JP | 2010019688 | 1/2010 |
| KR | 20070111649 | 11/2007 |
| WO | WO-03083480 | 10/2003 |
| WO | WO-2007064355 | 6/2007 |
| WO | WO-2009136869 | 11/2009 |
| WO | WO-2010088585 | 8/2010 |
| WO | WO-2010126640 | 11/2010 |
| WO | WO-2011133143 | 10/2011 |
| WO | WO-2011133144 | 10/2011 |

OTHER PUBLICATIONS

Hu, Min et al., Supporting Information for: "Nano Gold Fingers for Molecule Trapping and Detection", J. Am. Chem Soc. 2010, (Aug. 26, 2010) 13 pgs.

Huang, Fumin et al., "Actively Tuned Plasmons on Elastomerically Driven Au Nanoparticle Dimers", American Chemical society, (May 12, 2010) 6 pgs.

International Search Report and Written Opinion, Jul. 1, 2011. PCT Application No. PCT/US2010/053304.

International Search Report and Written Opinion, Jul. 1, 2011. PCT Application No. PCT/US2010/053343.

Penner, Reginald M., "Nanowire Arrays for Chemical Sensing", Univ. Of California, Irvine. PITTCON 2003, Mar. 9-14, Orlando, Florida. Abstract 950-5.

Baldwin, Jean, Norbert Schuhler, Ian S. Butler, & Mark P. aNDREWS, "Integrated Optics Evanescent Wave Surface Enhanced Raman Scattering (IO-EWSERS) of Mercaptopyridines on a Planar Optical Chemical Bench: Binding of Hydrogen and Copper Ion", Langmuir, 1996, vol. 12, pp. 6389-6398.

Chen, S.Y. et al., Raman Antenna Formed by Molecule/plasmonic Nanostructure Hybrid System, (Research Paper), Conference Paper, Quantum Electronics and Laser Science Conference, May 1, 2011, Baltimore, Maryland.

(56) References Cited

OTHER PUBLICATIONS

Cubukcu, E., et al., "Plasmonic Laser Antennas and Related Devices", IEEE Journal of Selected Topics in Quantum Electronics, Nov./Dec. 2008, vol. 14, No. 6, pp. 148-1461.

Du, Y. et al., SERS Enhancement1 Dependence on the Diameter and Aspect Ratio of Silver-nanowire Array Fabricated by Anodic Aluminium Oxide Template, (Research Paper), Applied Surface Science, Dec. 30, 2008, pp. 1901-1905, vol. 255, No. 5.

Fan et al., "Multilayer Silver Nanoparticles Modified Optical Fiber Tip for High Performance SERS Remote Sensing," 217th ECS Meeting—Vancouver, Canada, Apr. 25-30, 2010, J2—Electrochemical Nano/Bio Sensors 2, Abs# 1830.

Fan, J. G. et al., "Integrating Aligned Nanorod Array onto Optical Fibers for SERS Probes," Proc. of SPIE- Nanoengineering: Fabrication, Properties, Optics, and Devices III, vol. 6327, 2006, pp. R-1 to R10.

Gopinath, Ashwin, et al., Deterministic Aperiodic Arrays of Metal Nanoparticles for Surface-enhanced Raman Scattering (SERS), Publication Date: Mar. 2, 2009; vol. 17; On pp. 3741-3753. < http://www.bio-page.org/boriskina/Boriskina_OE2009.pdf>.

Guieu, Valérie, et al. "Multitip-localized enhanced Raman scattering from a nanostructured optical fiber array." The Journal of Physical Chemistry C 113.3 (2008): 874-881.

International Search Report, Mar. 30, 2011, PCT Application No. PCT/US2010/044039, Filed Jul. 30, 2010.

Josef Giglmayr, "Nano-Finger Electrodes for the Electro-Optical Generation and Tuning of Gratings at Several Wavelengths", <http://www.ipme.ru/ipme/conf/NN2003/NN2003_Abstracts.pdf > Publication Date: Aug. 30, 2003—Sep. 6, 2003.

Krishnamoorthy, Sivashankar, et al., Combining Micelle Self-assembly with Nanostencil Lithography to Create Periodic/aperiodic Micro-/nanopatterns on Surfaces, Publication Date: Jul. 30, 2008; vol. 20; On pp. 3533-3538. < http://onlinelibrary.wiley.com/doi/10.1002/adma.200702478/abstract >.

Levy, et al.; Department of Computer Sciences, University of TX at Austin, ACM Computing Surveys; vol. 22, No. 4; Dec. 1990; pp. 323-374.

Lucotti et al., "Fiber-optic SERS sensor with optimized geometry," Elsevier, ScienceDirect, Sensors and Actuators B, vol. 121, 2007, 356-364.

Morris, et al.; A Distributed Personal Computer Environment; Communications of the ACM ; vol. 29, No. 3; Mar. 1986; 29:184-201.

PCT International Search Report, Jan. 20, 2011, Hewlett-Packard Development Company, L.P. (PCT/US2010/031790, Filed Apr. 20, 2010).

PCT International Search Report, Dec. 23, 2010, Hewlett-Packard development Company, L.P. (PCT/US2010/031809, Filed Apr. 20, 2010).

Ren, Hongliang, et al. "The preparation of optical fibre nanoprobe and its application in spectral detection." Optics & Laser Technology 39.5 (2007): 1025-1029.

Segawa, H., et al., "Top-gathering pillar array of hybrid organic-inorganic material by means of self-organization", Applied Physics A—Materials Science & Processing, Mar. 17, 2006, vol. 83, pp. 447-451.

Weng, T.W. et al., Area Effect of Patterned Carbon Nanotube Bundle on Field Electron Emission Characteristics, (Research Paper), 9th International Conference on Atomically Con.

White, Daniel J., et al. "Nanostructured optical fibre for surface-enhanced Raman scattering sensing." Proc SPIE. vol. 7102. 2008.

Xie et al., "Polymer optical fiber SERS sensor with gold nanorods," Elsevier, Optics Communications, vol. 282, 2009, pp. 439-442.

Zhang et al., "Single-Fiber Probe Based on Surface Enhanced Raman Scattering (SERS)," IEEE Sensors, 2005, pp. 1088-1091.

500A

US 9,279,767 B2

CHEMICAL-ANALYSIS DEVICE INTEGRATED WITH METALLIC-NANOFINGER DEVICE FOR CHEMICAL SENSING

RELATED APPLICATIONS

This application is related to PCT Patent Application, Serial Number PCT/US10/31790 by Zhiyong Li, et al., filed on Apr. 20, 2010, entitled "MULTI-PILLAR STRUCTURE FOR MOLECULAR ANALYSIS," and assigned to the assignee of the present invention. This Application is also related to PCT Patent Application, Serial Number PCT/US10/31809 by Zhiyong Li, et al., filed on Apr. 20, 2010, entitled "A SELF-ARRANGING, LUMINESCENCE-ENHANCEMENT DEVICE FOR SURFACE-ENHANCED LUMINESCENCE," and assigned to the assignee of the present invention. This Application is also related to co-filed PCT Patent Application, Serial Number PCT/US10/53304 by Zhiyong Li, et al., filed on Oct. 20, 2010, entitled "METALLIC-NANOFINGER DEVICE FOR CHEMICAL SENSING," and assigned to the assignee of the present invention.

TECHNICAL FIELD

Examples of the present invention relate generally to metallic-nanofinger devices for chemical sensing.

BACKGROUND

Chemical-sensing techniques that employ surface-enhanced luminescence, such as surface-enhanced Raman spectroscopy (SERS), have emerged as leading-edge techniques for the analysis of the structure of complex organic molecules, in particular, biomolecules and even biological cells, viruses and their macromolecular components. For example, in SERS, scientists engaged in the application of Raman spectroscopy have found that it is possible to enhance the intensity of a Raman spectrum of a molecule. For example, by decorating a surface, upon which a molecule is later adsorbed, with a thin layer of a metal, surface plasmons are generated that have frequencies in the range of electromagnetic radiation emitted by such a molecule that enhance the intensity of the Raman spectrum of the molecule.

In addition, spectroscopists utilizing spectroscopic techniques for the analysis of molecular structures have a continuing interest in improving the sensitivity of their spectroscopic techniques. Not only is increased sensitivity useful for reducing the time of analysis, but also increased sensitivity can provide previously unachievable results. For example, increased sensitivity is directly related to lower detectability limits for previously undetected molecular constituents. Thus, scientists engaged in the application of surface-enhanced luminescence techniques are motivated to increase the sensitivity of surface-enhanced luminescence techniques, for example, SERS, for the detection of molecules and the spectral signatures of moieties in these molecules.

DESCRIPTION OF THE DRAWINGS

The accompanying drawings, which are incorporated in and form a part of this specification, illustrate examples of the invention and, together with the description, serve to explain the examples of the invention.

Figure 1:
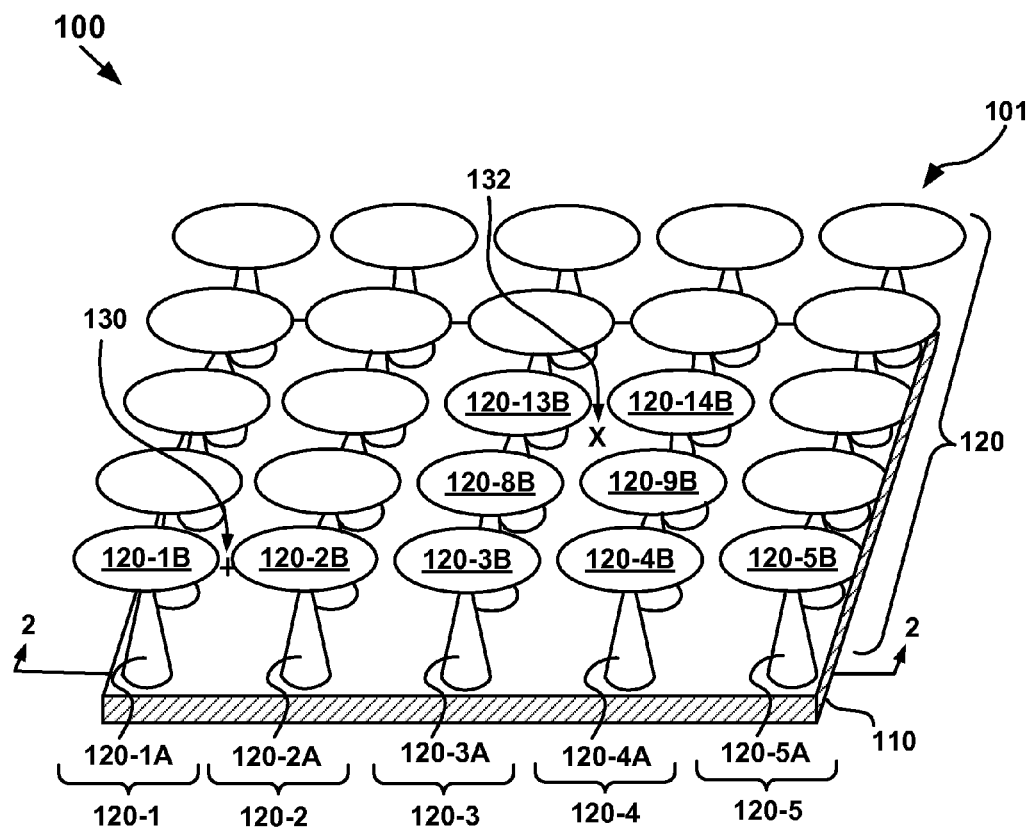
FIG. 1 is a perspective view of a metallic-nanofinger device for chemical sensing, in accordance with one or more examples of the present invention.

The drawings referred to in this description should not be understood as being drawn to scale except if specifically noted.

DESCRIPTION OF EXAMPLES

Reference will now be made in detail to the alternative examples of the present invention. While the invention will be described in conjunction with the alternative examples, it will be understood that they are not intended to limit the invention to these examples. On the contrary, the invention is intended to cover alternatives, modifications and equivalents, which may be included within the spirit and scope of the invention as defined by the appended claims.

Furthermore, in the following description of examples of the present invention, numerous specific details are set forth in order to provide a thorough understanding of the present invention. However, it should be noted that examples of the present invention may be practiced without these specific details. In other instances, well known methods, procedures, and components have not been described in detail as not to unnecessarily obscure examples of the present invention. Throughout the drawings, like components are denoted by like reference numerals, and repetitive descriptions are omitted for clarity of explanation if not necessary.

Examples of the present invention include a chemical-analysis device integrated with a metallic-nanofinger device for chemical sensing. The chemical-analysis device includes a metallic-nanofinger device, and a platform. The metallic-nanofinger device includes a substrate, and a plurality of nanofingers coupled with the substrate. A nanofinger of the plurality includes a flexible column, and a metallic cap coupled to an apex of the flexible column. At least the nanofinger and a second nanofinger of the plurality of nanofingers are to self-arrange into a close-packed configuration with at least one analyte molecule. A morphology of the metallic cap is to generate a shifted plasmonic-resonance peak associated with amplified luminescence from the analyte molecule. A method for using, and a chemical-analysis apparatus including the chemical-analysis device are also provided.

With reference now to FIG. 1, in accordance with one or more examples of the present invention, a perspective view 100 is shown of the metallic-nanofinger device 101 for chemical sensing. The metallic-nanofinger device 101 that provides for surface-enhanced luminescence includes the substrate 110, and the plurality 120 of nanofingers, for example, nanofingers 120-1, 120-2, 120-3, 120-4 and 120-5. The nanofinger 120-1 of the plurality 120 includes the flexible column 120-1A, and the metallic cap 120-1B. Similarly, other nanofingers, for example, nanofingers 120-2, 120-3, 120-4 and 120-5, of the plurality 120 include flexible columns, for example, flexible columns 120-2A, 120-3A, 120-4A and 120-5A, respectively, and metallic caps, for example, metallic caps 120-2B, 120-3B, 120-4B and 120-5B, respectively. As shown in FIG. 1, by way of example, a row of nanofingers includes nanofingers 120-1, 120-2, 120-3, 120-4 and 120-5, without limitation thereto; and, by way of example, an array of nanofingers includes several rows, without limitation thereto. Thus, in accordance with one example of the present invention, the plurality 120 of nanofingers includes the array of nanofingers including several rows of nanofingers. However, other arrangements of nanofingers that are less well-ordered than shown in FIG. 1 are also within the spirit and scope of examples of the present invention. The arrangement shown in FIG. 1 is illustrative of but one example of an arrangement of the plurality 120 of nanofingers in a metallic-nanofinger device 101 as may be fabricated in a top-down fabrication procedure, which employs a reticulated mask in a photolithographic process; but, other methods of fabrication are also within the spirit and scope of examples of the present invention, which are subsequently described. Moreover, the morphology of the metallic caps may differ from that shown in FIG. 1; for example, the morphology of the metallic caps may be substantially spherical, or alternatively, truncated substantially spherical, and the metallic caps themselves may be coated with a coating, in accordance with one or more examples of the present invention, which are also subsequently described.

With further reference to FIG. 1, in accordance with one or more examples of the present invention, a top portion including a metallic cap of a nanofinger, for example, nanofinger 120-1, of the plurality 120 of nanofingers may have the shape of an ellipsoid. However, in accordance with one or more examples of the present invention, a top portion including a metallic cap of a nanofinger is not limited to having the shape of an ellipsoid, as other shapes, in particular spheres as subsequently described, are also within the spirit and scope of examples of the present invention.

Figure 4:
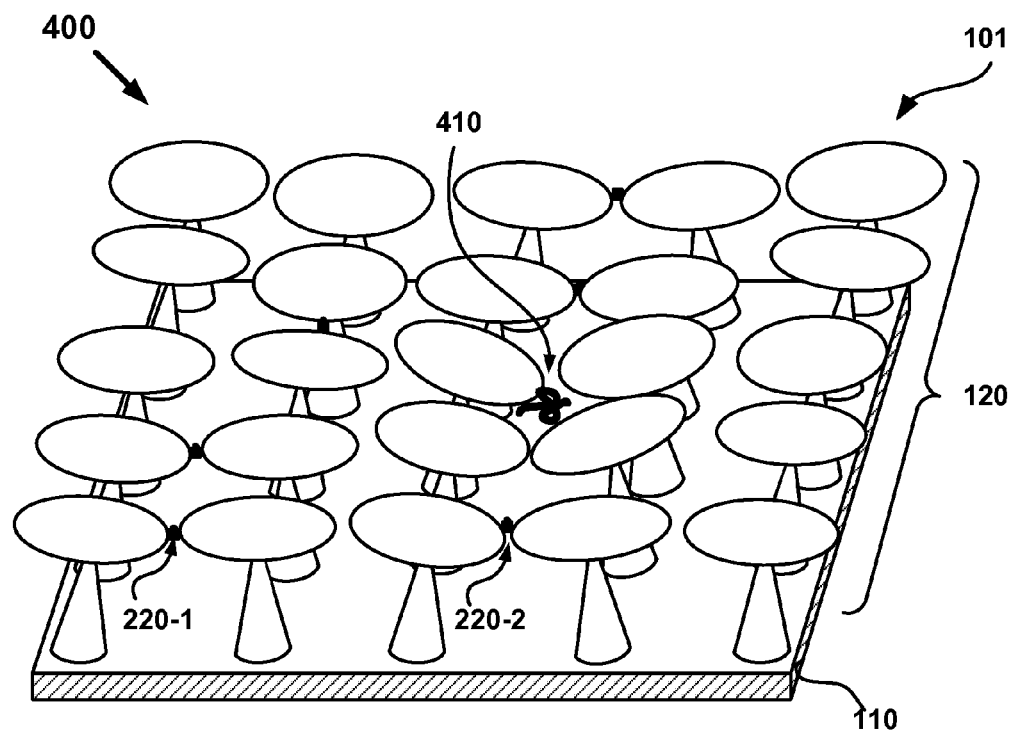
FIG. 4 is another perspective view of the metallic-nanofinger device for chemical sensing of FIG. 1 after the nanofingers have self-arranged into close-packed configurations with molecules disposed between the metallic caps, in accordance with one or more examples of the present invention.

With further reference to FIG. 1, by way of example, in accordance with one or more examples of the present invention, the flexible columns may have the form of nanocones, as shown in FIGS. 1 and 4, without limitation thereto; but, more generally, the flexible columns may be selected from the group consisting of: nanocones, nanopyramids, nanorods, nanobars, nanopoles and nanograss, without limitation thereto. As used herein, the terms of art, "nanocones," "nanopyramids," "nanorods," "nanobars," "nanopoles" and "nanograss," refer to structures that are substantially: conical, pyramidal, rod-like, bar-like, pole-like and grass-like, respectively, which have nano-dimensions as small as a few tens of nanometers (nm) in height and a few nanometers in diameter, or width. For example, flexible columns may include nanocolumns having the following dimensions: a diameter of 50 nm to 500 nm, a height of 50 nm to 2 micrometers (µm), and a gap between flexible columns of 20 nm to 500 nm. The terms of art, "substantially conical," "substantially pyramidal," "substantially rod-like," "substantially bar-like," "substantially pole-like" and "substantially grass-like," means that the structures have nearly the respective shapes of cones, pyramids, rods, bars, poles and grass-like asperities within the limits of fabrication with nanotechnology.

With further reference to FIG. 1, by way of example, in accordance with one or more examples of the present invention, the metallic caps may have the form of oblate nanoellipsoids, as shown in FIGS. 1 and 4, without limitation thereto; but, more generally, the metallic caps may be selected from the group consisting of: nanospheres, prolate nanoellipsoids, oblate nanoellipsoids, nanodisks, and nanoplates, without limitation thereto. As used herein, the terms of art, "nanospheres," "prolate nanoellipsoids," "oblate nanoellipsoids," "nanodisks," and "nanoplates," refer to structures that are substantially: spherical, prolate ellipsoidal, oblate ellipsoidal, disk-like, and plate-like, respectively, which have nano-dimensions as small as a few nanometers in size: height, diameter, or width. For example, in accordance with one or more examples of the present invention, the diameter of the metallic caps is on the order of 20 nm to 500 nm. In addition, the terms of art, "substantially spherical," "substantially prolate ellipsoidal," "substantially oblate ellipsoidal," "substantially disk-like," and "substantially and plate-like," means that the structures have nearly the respective shapes of spheres, prolate ellipsoids, oblate ellipsoids, disks, and plates within the limits of fabrication with nanotechnology.

With further reference to FIG. 1, in accordance with one or more examples of the present invention, the metallic cap 120-1B is coupled to an apex 120-1C (not shown in FIG. 1, but see FIGS. 5B and 5C) of the flexible column 120-1A. Similarly, other metallic caps, for example, metallic caps 120-2B, 120-3B, 120-4B and 120-5B, are coupled to apices, for example, apices 120-2C, 120-3C, 120-4C and 120-5C, respectively, (not shown in FIG. 1, but see FIGS. 5B and 5C) of flexible columns, for example, flexible columns 120-2A, 120-3A, 120-4A and 120-5A, respectively. As shown in FIG. 1, a plurality of interstices is disposed between the plurality 120 of nanofingers. For example, a small interstice 130 is located between metallic cap 120-1B and metallic cap 120-2B. By way of further example, an interstice of a different kind, a large interstice 132, is located between four metallic caps 120-8B, 120-9B, 120-13B and 120-14B. Such interstices are to receive analyte molecules (not shown, but see FIG. 2) for the purpose of surface-enhanced luminescence. As used herein, the term of art, "surface-enhanced luminescence," also embraces within the scope of its meaning surface-enhanced Raman emission, as in surface-enhanced Raman spectroscopy (SERS), surface-enhanced reflectivity, surface-enhanced light scattering, and surface-enhanced fluorescence. In accordance with one or more examples of the present invention, at least the nanofinger 120-1 and a second nanofinger 120-2 of the plurality 120 are to self-arrange into a close-packed configuration with at least one analyte molecule 220-1 (not shown, but see FIG. 2) disposed between at least the metallic cap 120-1B and a second metallic cap 120-2B of respective nanofinger 120-1 and second nanofinger 120-2, for example, at the location of the small interstice 130, as is next described with the aid of a cross-section through line 2-2.

Figure 2:
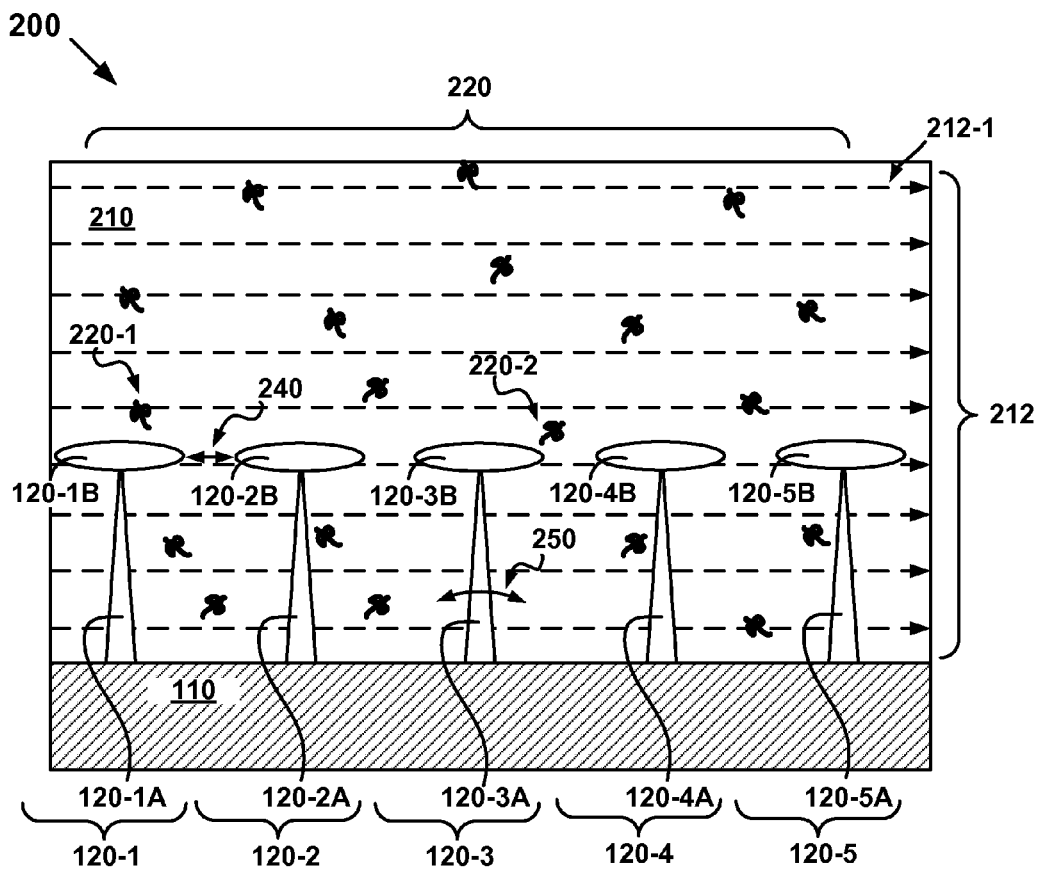
FIG. 2 is a cross-sectional elevation view, through line 2-2 of FIG. 1, of the metallic-nanofinger device for chemical sensing in contact with a liquid carrying a plurality of molecules, in accordance with one or more examples of the present invention.

With reference now to FIG. 2, in accordance with one or more examples of the present invention, a cross-sectional elevation view 200 is shown of the metallic-nanofinger device 101 for chemical sensing through line 2-2 of FIG. 1. FIG. 2 shows a row of nanofingers 120-1, 120-2, 120-3, 120-4 and 120-5 in profile; nanofingers 120-1, 120-2, 120-3, 120-4 and 120-5 include flexible columns 120-1A, 120-2A, 120-3A, 120-4A and 120-5A, and metallic caps 120-1B, 120-2B, 120-3B, 120-4B and 120-5B, respectively. As shown in FIG. 2, the range of flexibility of each of the flexible columns 120-1A, 120-2A, 120-3A, 120-4A and 120-5A is indicated by the example double headed arrow 250, which is shown overlaying flexible column 120-3A. As further shown in FIG. 2, the row of nanofingers 120-1, 120-2, 120-3, 120-4 and 120-5 of the metallic-nanofinger device 101 is to come into contact with a liquid 212 carrying a plurality 220 of analyte molecules, for example, analyte molecules 220-1 and 220-2. By way of example, as shown in FIG. 2, the liquid may be in motion, without limitation thereto, as indicated by flow vectors, of which flow vector 212-1 is an example; such a configuration might be suitable for sampling an environment with the metallic-nanofinger device 101 for the presence of a target molecule, also referred to herein as a "target," without limitation thereto.

With further reference to FIG. 2, as used herein, the term of art, "molecule," may be used to refer to the smallest unit of an element consisting of one or more like atoms, the smallest unit of a compound consisting of one or more like or different atoms, and more generally to any very small particle, for example, a biological cell, a virus, or molecular component of a biological cell or a virus. Also, as used herein the term of art, "target," also includes an analyte molecule selected from the group consisting of molecules, organic molecules, biomolecules, biological cells, viruses and the molecular components of biological cells and viruses. Alternatively, the liquid may be static without motion, as might be the case for immersion of the metallic-nanofinger device 101 in a solution containing an analyte including the liquid and molecules, also more generally analyte molecules, of which the analyte is composed. Thus, the metallic-nanofinger device 101 is to receive molecules, also more generally analyte molecules, of an analyte for spectroscopic analysis as is SERS, surface-enhanced fluorescence spectroscopy, surface-enhanced reflectivity, surface-enhanced light scattering, or other surface-enhanced luminescence applications.

With further reference to FIG. 2, in accordance with one or more examples of the present invention, an analyte molecule 220-1 may approach the site of an interstice, for example, small interstice 130, where adjacent metallic caps, for example, metallic caps 120-1B and 120-2B, are separated by a distance 240. In accordance with an example of the present invention, a metallic cap, for example, metallic cap 120-1B, of the plurality 120 of nanofingers is to bind to a analyte molecule 220-1 disposed in close proximity to the metallic cap 120-1B. By way of example, such binding may occur through Van der Waals forces between the metallic cap 120-1B and the analyte molecule 220-1, without limitation thereto; or alternatively, such binding may occur through other types of binding forces, such as surface physisorption or surface chemisorption of the molecule by the metallic cap 120-1B, without limitation thereto. Once the molecule is bound to the metallic cap, for example, metallic cap 120-1B, in accordance with an example of the present invention, at least one metallic cap, for example, metallic cap 120-1B, of a plurality 530 (see FIG. 5C) of metallic caps is to enhance luminescence from the analyte molecule 220-1 disposed in close proximity to the metallic cap 120-1B. Moreover, in accordance with another example of the present invention, at least one metallic cap, for example, metallic cap 120-1B, of the plurality 530 (see FIG. 5C) of metallic caps may be composed of a constituent that enhances surface luminescence, such as a material selected from the group consisting of copper, silver, aluminum and gold, or any combination of copper, silver, aluminum and gold. Furthermore, in accordance with another example of the present invention, the flexible columns 120-1A, 120-2A, 120-3A, 120-4A and 120-5A of the plurality 120 of nanofingers 120-1, 120-2, 120-3, 120-4 and 120-5 further include a flexible material selected from the group, which includes both dielectric and non-dielectric materials, consisting of a highly cross-linked uv-curable or thermal-curable polymer, a highly cross-linked uv-curable or thermal-curable plastic, a polysiloxane compound, silicon, silicon dioxide, spin-on glass, a sol-gel material, silicon nitride, diamond, diamond-like carbon, aluminum oxide, sapphire, zinc oxide, and titanium dioxide, the purpose of which is next described.

Figure 3:
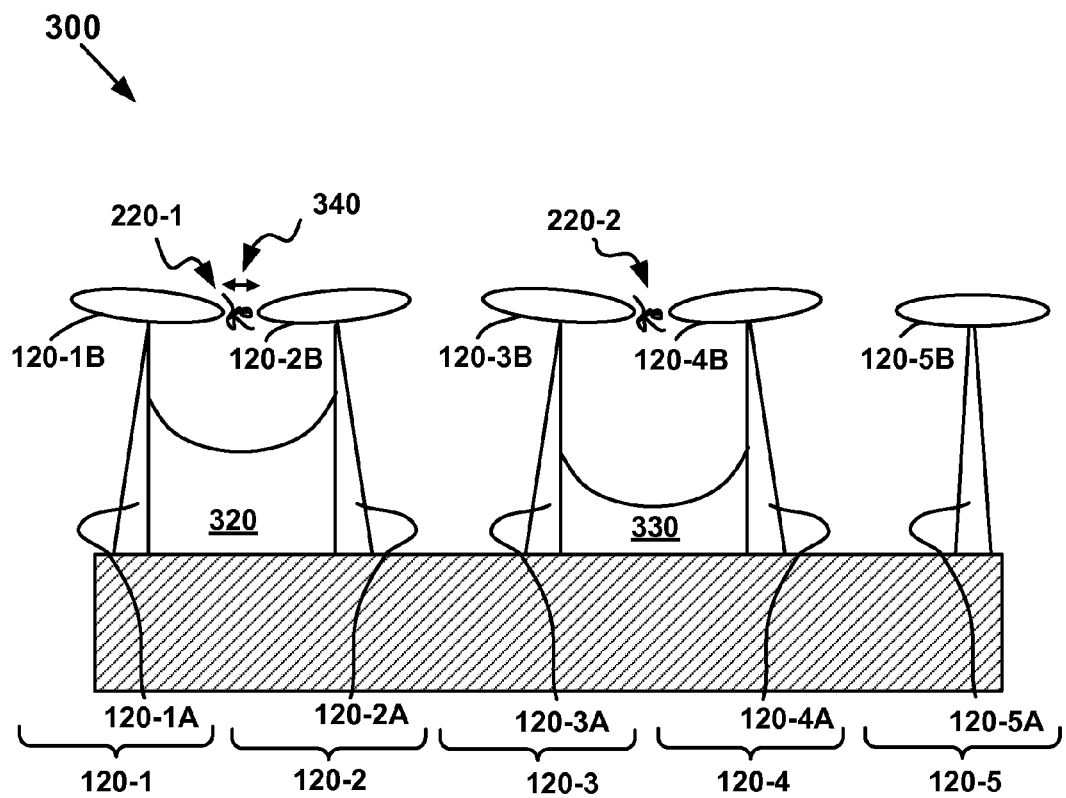
FIG. 3 is a cross-sectional elevation view, through line 2-2 of FIG. 1, of the metallic-nanofinger device for chemical sensing that shows nanofingers self-arranging into close-packed configurations with molecules disposed between metallic caps of nanofingers, in accordance with one or more examples of the present invention.

With reference now to FIG. 3, in accordance with one or more examples of the present invention, a cross-sectional elevation view 300 is shown of the metallic-nanofinger device 101 for chemical sensing through line 2-2 of FIG. 1. FIG. 3 shows nanofingers 120-1, 120-2, 120-3 and 120-4 self-arranging into close-packed configurations with analyte molecules, for example, analyte molecule 220-1, disposed between metallic caps 120-1B and 120-2B of the nanofingers 120-1 and 120-2, respectively, and analyte molecule 220-2, disposed between metallic caps 120-3B and 120-4B of the nanofingers 120-3 and 120-4, respectively. Because the flexible columns 120-1A, 120-2A, 120-3A and 120-4A of the plurality 120 of nanofingers include a flexible, or compliant, material as described above, in accordance with an example of the present invention, at least one flexible column 120-1A is to bend towards at least a second flexible column 120-2A, and to dispose the analyte molecule 220-1 in close proximity with at least a second metallic cap 120-2B on the second flexible column 120-2A. Liquid pools 320 and 330, may remain trapped between the flexible columns, for example, flexible columns 120-1A and 120-2A, and flexible columns 120-3A and 120-4A, respectively, which give rise to microcapillary forces exerted upon the flexible columns; the microcapillary forces serve to draw together the flexible columns, for example, flexible columns 120-1A and 120-2A, and flexible columns 120-3A and 120-4A, as the liquid evaporates, which allows the nanofingers 120-1 and 120-2 to self-arrange into a close-packed configuration with at least one analyte molecule 220-1 disposed between at least the metallic cap 120-1B and a second metallic cap 120-2B of respective nanofinger 120-1 and second nanofinger 120-2.

Thus, with further reference to FIG. 3, in accordance with one or more examples of the present invention, the flexible column 120-1A is to bend towards the second flexible column 120-2A under action of microcapillary forces induced by removal of liquid carrier 210 provided to carry the analyte molecule 220-1 into proximity with the metallic cap 120-1B and second metallic cap 120-2B. In accordance with another example of the present invention, a spacing 340 of the close-packed configuration between the metallic cap 120-1B and second metallic cap 120-2B with a analyte molecule 220-1 disposed between the metallic cap 120-1B and second metallic cap 120-2B is determined by a balance of binding forces, between the analyte molecule 220-1 and the metallic cap 120-1B and second metallic cap 120-2B, with restoring forces exerted by the flexible column 120-1A and second flexible column 120-2A due to displacement of the flexible column 120-1A and second flexible column 120-2A towards the analyte molecule 220-1. Thus, in accordance with an example of the present invention, the spacing 340 approaches a limit determined by the size of the analyte molecule 220-1, which may be as small as 0.5 nm. The spacing 340 approaches the physical limit of the smallest possible separation between metallic caps 120-1B and 120-2B; and, thus, the metallic caps act as two antennas approaching the largest coupling that may be possible between at least two such antennas for surface-enhanced luminescence. Moreover, the effect of coupling more than two antennas is also within the spirit and scope examples of the present invention, which is next described.

With reference now to FIG. 4 and further reference to FIGS. 1 and 3, in accordance with one or more examples of the present invention, another perspective view 400 is shown of the metallic-nanofinger device 101 for chemical sensing of FIG. 1. As shown in FIG. 4, most of the nanofingers of the plurality 120 have self-arranged into close-packed configurations with analyte molecules, for example, analyte molecules 220-1, 220-2 and 410, disposed between the metallic caps, for example, metallic caps 120-1B and 120-2B, metallic caps 120-3B and 120-4B, and metallic caps 120-8B, 120-9B, 120-13B and 120-14B, respectively. In accordance with one or more examples of the present invention, the corresponding flexible columns coupled with the metallic caps have bent towards adjacent flexible columns, as might occur under action of microcapillary forces induced by removal of the liquid carrier 210. For example, the small interstices, similar to small interstice 130, are to capture smaller analyte molecules, for example, analyte molecules 220-1 and 220-2; and, the large interstices, similar to large interstice 132, are to capture larger analyte molecules, for example, analyte molecule 410. In accordance with one or more examples of the present invention, the size of the analyte molecules captured is determined by the self-arranging spacing between the metallic caps, for example, the spacing 340 of the close-packed configuration between the metallic cap 120-1B and second metallic cap 120-2B with the analyte molecule 220-1 disposed between the metallic cap 120-1B and second metallic cap 120-2B. By way of example, in accordance with one or more examples of the present invention, the size of the self-arranging spacing may be on the order of 2 nm, without limitation thereto. Thus, in accordance with one or more examples of the present invention, the metallic-nanofinger device 101 may be to provide a device for the capture of analyte molecules of various sizes from a solution carrying an analyte of at least one particular molecular species. For example, the metallic-nanofinger device 101 may then be used in SERS analysis of the captured molecules of an analyte, which is subsequently described in greater detail.

Figure 5A:
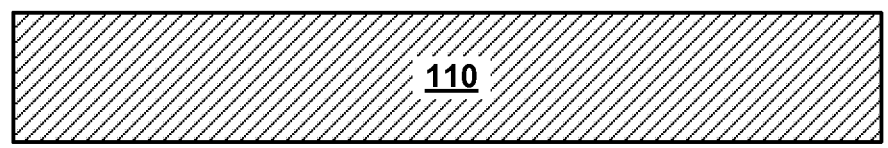
FIGS. 5A, 5B and 5C are cross-sectional elevation views at various stages in the fabrication of the metallic-nanofinger device for chemical sensing of FIG. 1 illustrating a sequence of processing operations used in fabrication, in accordance with one or more examples of the present invention.
Figure 5B:
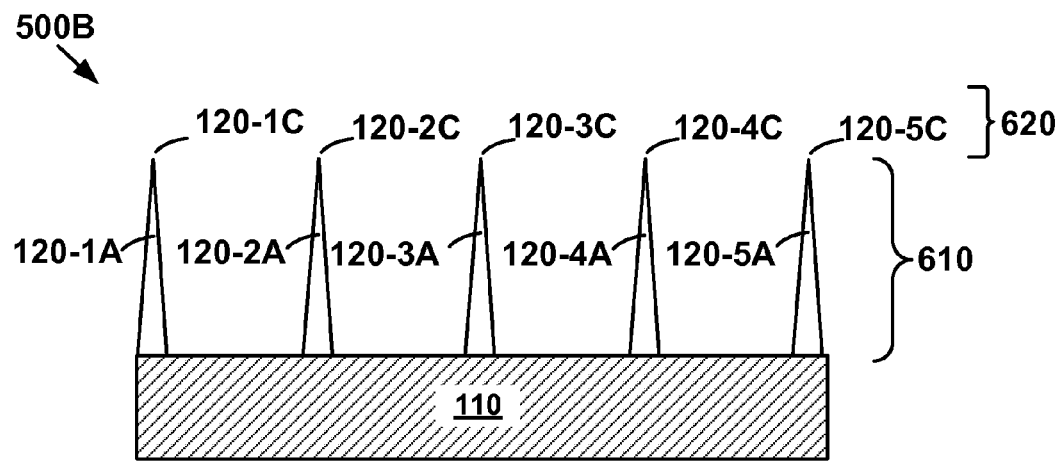
Figure 5C:
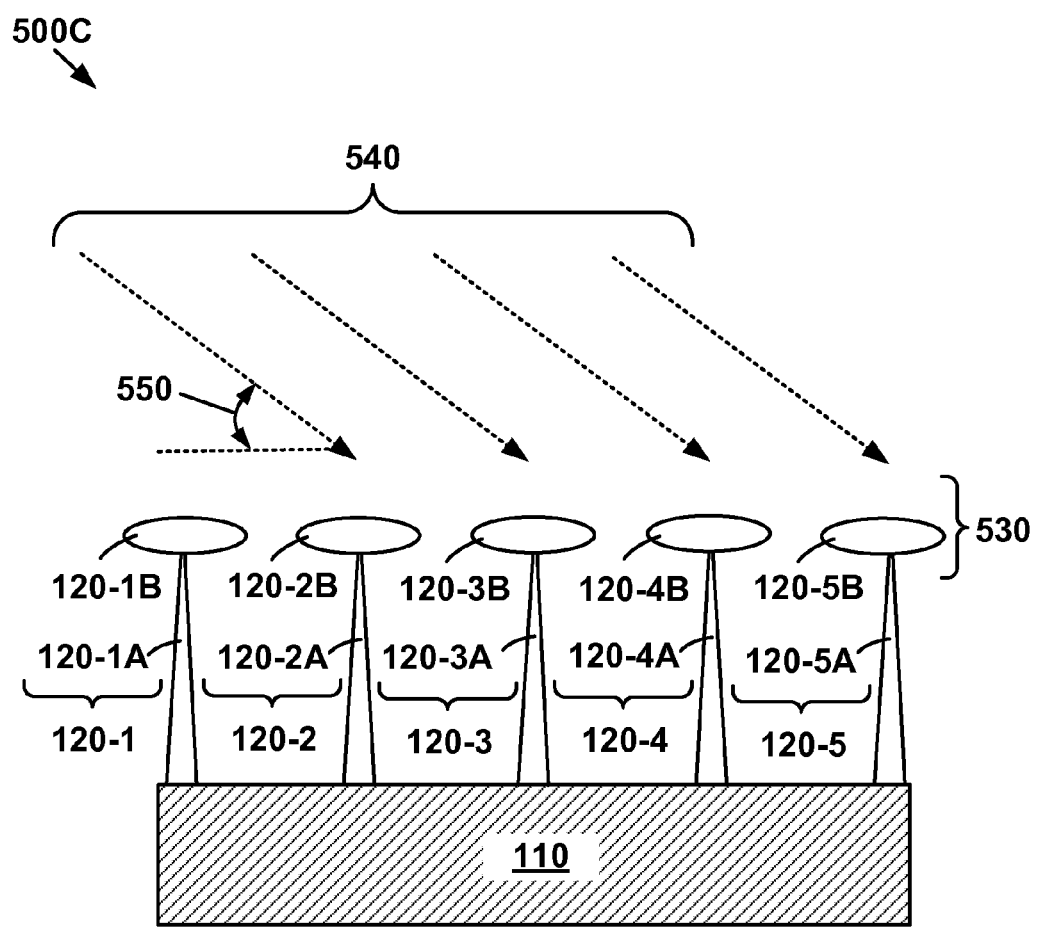

With reference now to FIGS. 5A, 5B and 5C, in accordance with yet other examples of the present invention, cross-sectional elevation views 500A, 500B and 500C, respectively, are shown of the metallic-nanofinger device 101 for chemical sensing of FIG. 1 at various stages of fabrication of the metallic-nanofinger device 101. FIGS. 5A, 5B and 5C illustrate a sequence of processing operations used in fabrication of the metallic-nanofinger device 101. FIG. 5A shows the substrate 110 upon which the rest of the structure of the metallic-nanofinger device 101 is fabricated. In accordance with one or more examples of the present invention, the substrate may be a material selected from the group consisting of silicon, glass, quartz, silicon nitride, sapphire, aluminum oxide, diamond, diamond-like carbon, one or more plastics, and one or more metals and metallic alloys. In accordance with one or more examples of the present invention, the substrate may be in a form selected from the group consisting of a sheet, a wafer, a film and a web. For example, if the substrate is in the form of a web, the substrate may be used as feed stock, as rolls of material in a roll-to-roll fabrication process. For another example, the substrate may be in the form of a flexible polymer film composed of a plastic material, such as polyimide, polyethylene, polypropylene, or some other suitable polymeric plastic. Thus, in accordance with one or more examples of the present invention, the substrate may be either rigid, as for a semiconductor wafer, or flexible, as for the web.

With further reference now to FIGS. 5B and 1, in accordance with one or more examples of the present invention, a cross-sectional elevation view 500B is shown of the metallic-nanofinger device 101 for chemical sensing of FIG. 1 at an intermediate stage of fabrication. FIG. 5B shows a plurality 510 of flexible columns, for example, flexible columns 120-1A, 120-2A, 120-3A, 120-4A and 120-5A, on the substrate 110. Each of the flexible columns of the plurality 510 of flexible columns, for example, flexible columns 120-1A, 120-

2A, 120-3A, 120-4A and 120-5A, includes an apex of a plurality 520 of apices, for example, apices 120-1C, 120-2C, 120-3C, 120-4C and 120-5C. In accordance with one or more examples of the present invention, the plurality 510 of flexible columns may be produced utilizing a process selected from the group consisting of growing nanowires on the substrate 110, etching the substrate 110, nano-imprinting a coating on the substrate 110, and hot nano-embossing a coating on the substrate 110. For example, in growing nanowires to produce the flexible columns, nanowire seeds are deposited onto the substrate 110, for example, silicon; and, the nanowire is grown during chemical vapor deposition from silane. By way of another example, in etching the substrate to produce the flexible columns, a reactive ion etching (RIE) process is applied to the substrate 110, for example, silicon; and, flexible columns, for example, in the form of nanocones, without limitation thereto, are produced by removing material from the substrate 110 through the action of reactive gaseous molecules, such as, fluorine, chlorine, bromine, or a halogen molecules, in the presence of gaseous nitrogen, argon, or oxygen molecules. By way of yet another example, in nanoimprinting the substrate to produce the flexible columns, a highly viscous thin film, for example, a highly cross-linked polymer, is applied to the substrate 110, for example, in the form of a web, to produce a coating on the web; and, flexible columns, for example, in the form of nanopoles, without limitation thereto, are produced by rolling the web between a pair of rolls, one of which is a die having a relief pattern that is impressed into the highly viscous thin film coating of the web leaving a negative of the relief pattern of the die in the form of a plurality of nanopoles on the web, substrate 110. By way of yet a further example, in hot nano-embossing a coating on the substrate 110, a polymer, or plastic, is applied to the substrate 110 to produce a coating on the substrate 110; and, flexible columns, for example, in the form of nanopoles, without limitation thereto, are produced by hot embossing the coating with a die, which has a relief pattern that is impressed into the polymer, or plastic, that coats the substrate 110 leaving a negative of the relief pattern of the die in the form of a plurality of nanopoles on the substrate 110.

With further reference now to FIGS. 5C and 1, in accordance with one or more examples of the present invention, a cross-sectional elevation view 500C is shown of the metallic-nanofinger device 101 for chemical sensing of FIG. 1 nearing a final stage in fabrication. FIG. 5C shows a plurality 120 of nanofingers, for example, nanofingers 120-1, 120-2, 120-3, 120-4 and 120-5, on the substrate 110. Each of the nanofingers, for example, nanofingers 120-1, 120-2, 120-3, 120-4 and 120-5, includes the flexible column of the plurality 510 of flexible columns, for example, flexible columns 120-1A, 120-2A, 120-3A, 120-4A and 120-5A, and the metallic cap of the plurality 530 of metallic caps, for example, metallic caps 120-1B, 120-2B, 120-3B, 120-4B and 120-5B, such that each metallic cap is disposed upon an apex of the plurality 520 of apices, for example, apices 120-1C, 120-2C, 120-3C, 120-4C and 120-5C, respectively. In accordance with one or more examples of the present invention, the plurality 120 of nanofingers may be produced utilizing a process selected from the group consisting of evaporating a metallic cap, for example, metallic cap 120-1B, electroplating a metallic cap, precipitating a metallic cap from a colloidal suspension of metallic nanoparticles, lifting-off portions of a deposited metallic layer to form a metallic cap, and reducing adsorbed metalo-organic compounds by energetic particle bombardment to form a metallic cap.

For example, with further reference to FIGS. 5C and 1, in accordance with one or more examples of the present invention, in evaporating to produce the metallic caps, a stream of metal vapor 540 is produced, using thin-film vacuum-evaporation techniques, to deposit metal onto the plurality 520 of apices of the plurality 510 of flexible columns 120-1A, 120-2A, 120-3A, 120-4A and 120-5A. The plurality 530 of metallic caps 120-1B, 120-2B, 120-3B, 120-4B and 120-5B are grown from the metal vapor depositing metal onto the plurality 520 of apices 120-1C, 120-2C, 120-3C, 120-4C and 120-5C of the plurality 510 of flexible columns 120-1A, 120-2A, 120-3A, 120-4A and 120-5A. In accordance with one or more examples of the present invention, fabricating the plurality 530 of metallic caps may include evaporating metal at an angle 550 of about 30° to a surface of the substrate 110 onto the plurality 520 of apices 120-1C, 120-2C, 120-3C, 120-4C and 120-5C of the plurality 510 of flexible columns 120-1A, 120-2A, 120-3A, 120-4A and 120-5A. Moreover, in accordance with one or more examples of the present invention, the size, and consequently the spacing, of the metallic caps 120-1B, 120-2B, 120-3B, 120-4B and 120-5B can be controlled by limiting the amount of material deposited from the metallic vapor during the evaporation process.

By way of another example, with further reference to FIGS. 5C and 1, in accordance with one or more examples of the present invention, in electroplating a metallic cap, the substrate 110 including the flexible columns 120-1A, 120-2A, 120-3A, 120-4A and 120-5A is immersed in a plating solution containing metal cations. An electrical potential is applied to the substrate 110 including the flexible columns 120-1A, 120-2A, 120-3A, 120-4A and 120-5A, which results in an enhanced electrical field at the apices, for example, apex 120-1C, of the flexible columns, for example, flexible column 120-1A. The enhanced electrical field attracts the metal cations to the apices, for example, apex 120-1C, of the flexible columns, for example, flexible column 120-1A, where chemical reduction of the metal cations occurs and metal is deposited to grow the metallic caps, for example, metallic cap 120-1B.

Similarly, by way of another example, with further reference to FIGS. 5C and 1, in accordance with one or more examples of the present invention, in precipitating metallic caps from a colloidal suspension of metallic nanoparticles, the substrate 110 including the flexible columns 120-1A, 120-2A, 120-3A, 120-4A and 120-5A is immersed in a colloidal suspension of metallic nanoparticles; an electrical potential is applied to the substrate 110 including the flexible columns 120-1A, 120-2A, 120-3A, 120-4A and 120-5A, which results in an enhanced electrical field at the apices, for example, apex 120-1C, of the flexible columns, for example, flexible column 120-1A; the enhanced electrical field attracts metallic nanoparticles from the colloidal suspension to the apices, for example, apex 120-1C, of the flexible columns, for example, flexible column 120-1A, where the metallic nanoparticles are deposited to grow the metallic caps, for example, metallic cap 120-1B.

By way of yet another example, with further reference to FIGS. 5C and 1, in accordance with one or more examples of the present invention, in a lift-off process for lifting-off portions of a deposited metallic layer to produce the metallic caps, a layer of photoresist is applied to the substrate 110 including the flexible columns 120-1A, 120-2A, 120-3A, 120-4A and 120-5A. An undercut structure is produced in the photoresist adjacent to the sides of the columns, and the photoresist is etched away from the apices 120-1C, 120-2C, 120-3C, 120-4C and 120-5C of the flexible columns 120-1A, 120-2A, 120-3A, 120-4A and 120-5A. The stream of metal vapor 540 is deposited, using thin-film deposition techniques, for example, sputtering or evaporation, onto the plurality 520 of apices of the plurality 510 of flexible columns 120-1A, 120-2A, 120-3A, 120-4A and 120-5A. A thin film is deposited over the surface of the combined photoresist and partially fabricated metallic-nanofinger device 101. The photoresist and portions of the metal layer adhering to the photoresist between the flexible columns 120-1A, 120-2A, 120-3A, 120-4A and 120-5A is then removed and the plurality 530 of metallic caps 120-1B, 120-2B, 120-3B, 120-4B and 120-5B is left adhering to the plurality 520 of apices 120-1C, 120-2C, 120-3C, 120-4C and 120-5C of the plurality 510 of flexible columns 120-1A, 120-2A, 120-3A, 120-4A and 120-5A.

By way of yet a further example, with further reference to FIGS. 5C and 1, in accordance with one or more examples of the present invention, in reducing adsorbed metalo-organic compounds by energetic particle bombardment to produce the metallic caps 120-1B, 120-2B, 120-3B, 120-4B and 120-5B, the substrate 110 including the flexible columns 120-1A, 120-2A, 120-3A, 120-4A and 120-5A is exposed to a vapor of a chemical compound bearing a metal moiety, for example, a metalo-organic compound as used in chemical vapor deposition (CVD). For example, the metalo-organic compound may be provided in the form of a gas admitted to a vacuum chamber, such as, the vacuum chamber of a focused-ion beam (FIB) tool, a scanning electron microscope (SEM), or the target chamber of a laser ablation system, without limitation thereto. A suitable gas-injection system (GIS) interfaced to the vacuum chamber may be used to provide the chemical vapor bearing a metal moiety, for example, the metalo-organic compound. The gaseous vapor of the metalo-organic compound adsorbs on the surface of the substrate 110 including the apices 120-1C, 120-2C, 120-3C, 120-4C and 120-5C of the flexible columns 120-1A, 120-2A, 120-3A, 120-4A and 120-5A. An energetic beam of particles, for example, ions, electrons, or photons, without limitation thereto, irradiates the apices 120-1C, 120-2C, 120-3C, 120-4C and 120-5C of the flexible columns 120-1A, 120-2A, 120-3A, 120-4A and 120-5A. Such energetic beams of particles, for example, ions, electrons, or photons, without limitation thereto, may be provided, for example, by: the ion gun of a FIB tool, the electron gun of an SEM, or a laser of a laser ablation system, without limitation thereto. The energetic beam of particles, for example, ions, electrons, or photons, without limitation thereto, reduces the adsorbed gaseous vapor of the metalo-organic compound and grows the plurality 530 of metallic caps 120-1B, 120-2B, 120-3B, 120-4B and 120-5B onto the plurality 520 of apices 120-1C, 120-2C, 120-3C, 120-4C and 120-5C of the plurality 510 of flexible columns 120-1A, 120-2A, 120-3A, 120-4A and 120-5A.

Figure 6A:
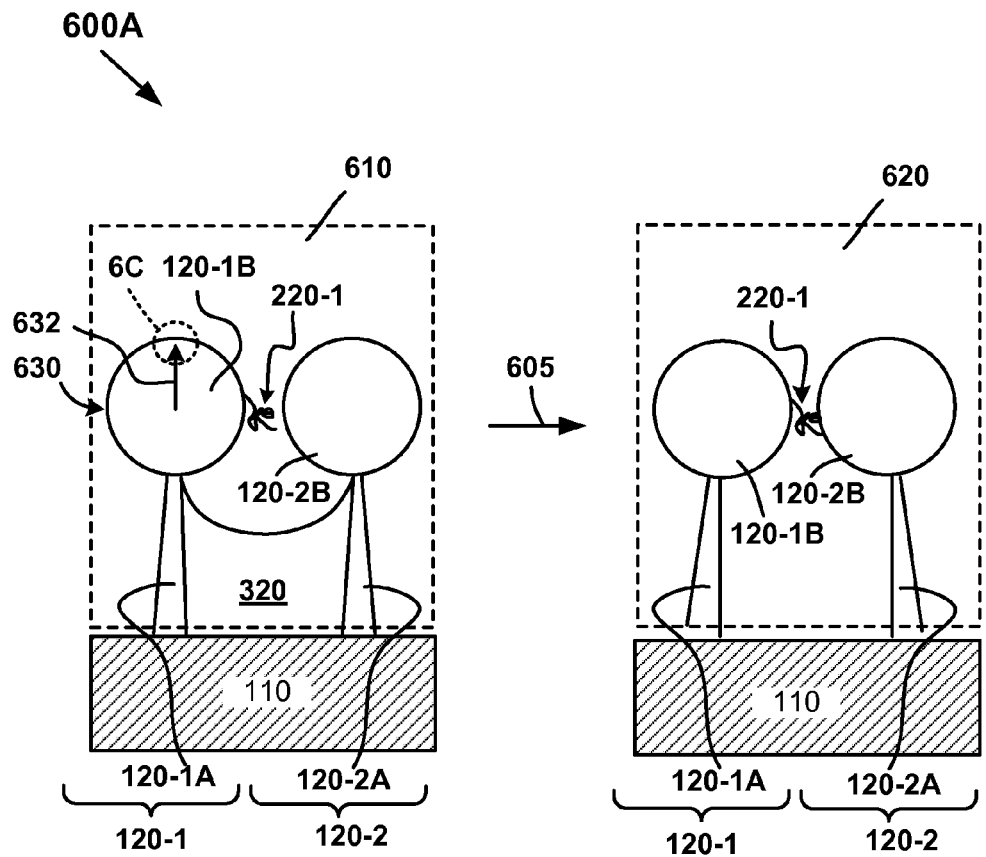
FIG. 6A is a cross-sectional elevation view, similar to that of FIG. 3, of the metallic-nanofinger device for chemical sensing having nanofingers with a substantially spherical metallic cap that schematically shows a change in configuration of the nanofingers upon self-arranging into a close-packed configuration, in accordance with one or more examples of the present invention.

With reference now to FIG. 6A, in accordance with one or more examples of the present invention, a cross-sectional elevation view 600A of a portion of the metallic-nanofinger device 101 for chemical sensing is shown. FIG. 6A shows a first configuration 610 of nanofingers 120-1 and 120-2 after wetting with the liquid 212 and upon formation of liquid pool 320. FIG. 6A also shows a second configuration 620 of nanofingers 120-1 and 120-2 after removal of the liquid 212 and self-arranging of nanofingers 120-1 and 120-2 into a close-packed configuration. At least one analyte molecule 220-1 may be disposed between at least the metallic cap 120-1B and a second metallic cap 120-2B of respective nanofinger 120-1 and second nanofinger 120-2. Thus, FIG. 6A schematically shows the change in configuration from first configuration 610 to second configuration 620 with the operation of purging the metallic-nanofinger device 101 of liquid 212, indicated by arrow 605. The metallic-nanofinger device 101 includes the substrate 110 and the plurality 120 of nanofingers; component parts of the nanofingers 120-1 and 120-2 are arranged as previously described in the discussion of FIG. 1. However, with reference also to FIGS. 6B and 6C, in one or more examples of the present invention, a morphology of the metallic cap 120-1B is to generate a shifted plasmonic-resonance peak 622 with enhanced amplitude 626 associated with amplified luminescence from the analyte molecule 220-1. The circled portion 6C of metallic cap 120-1B serves to detail the morphology of the metallic cap 120-1B with respect to a surface 630 of the metallic cap 120-1B and a shape parameter for the metallic cap 120-1B, which is shown in FIG. 6A as an average radius 632 of a substantially spherical metallic cap 120-1B. As used herein, the terms of art, "substantially spherical," and "truncated substantially spherical," with respect to the metallic cap 120-1B refers to the sphericity of the metallic cap 120-1B that can be achieved through one of the fabrication processes previously described in the discussion of FIGS. 5A-5C.

Figure 6B:
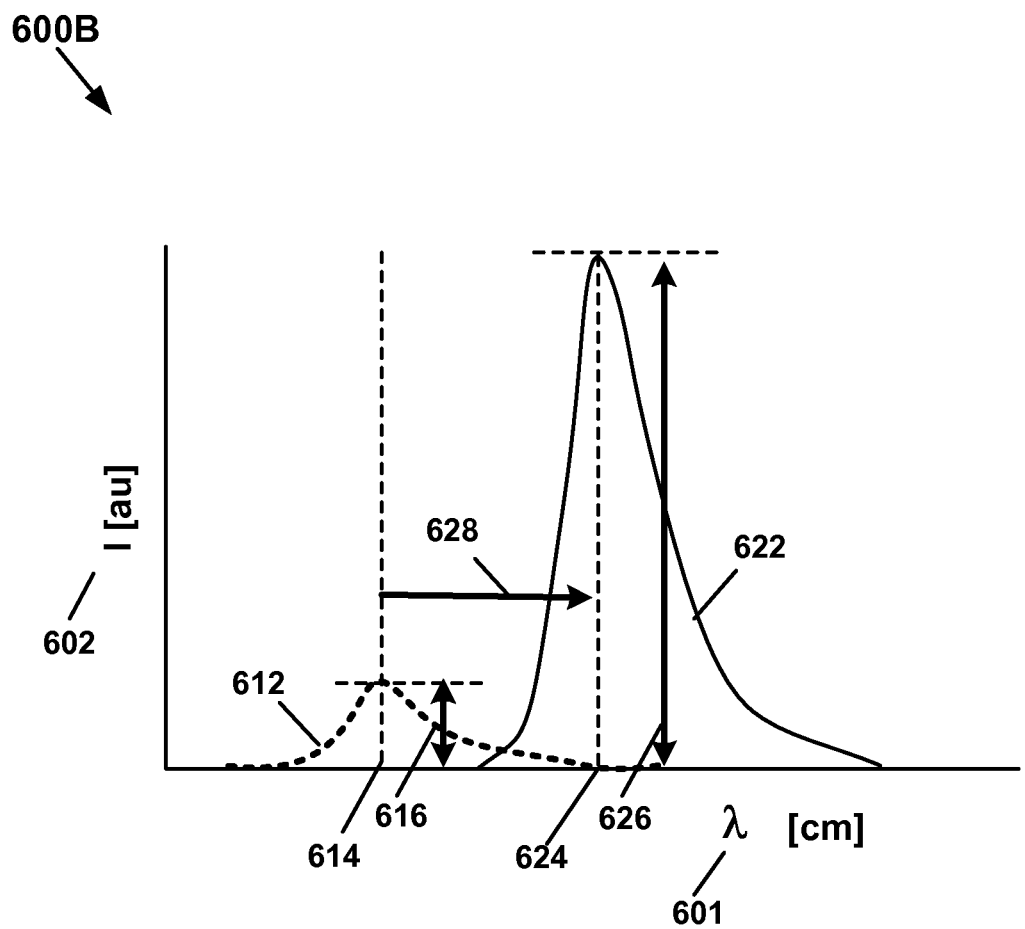
FIG. 6B is a plot that shows the enhancement of the amplitude of a plasmonic-resonance peak with shifting to longer wavelengths upon self-arranging of the nanofingers of FIG. 6A into a close-packed configuration, in accordance with one or more examples of the present invention.

With reference now to FIG. 6B, in accordance with one or more examples of the present invention, a plot 600B is shown that illustrates generation of the shifted plasmonic-resonance peak 622 with enhanced amplitude 626 with shifting to longer wavelengths. The enhancement of the amplitude 626 occurs upon self-arranging of the nanofingers, for example, nanofingers 120-1 and 120-2, into close-packed configurations, of which second configuration 620 of FIG. 6A is one example. The plot 600B shows the intensity 602, in arbitrary units (au), as a function of wavelength 601, in units of centimeters (cm), of both a plasmonic-resonance peak 612 associated with first configuration 610 of FIG. 6A, and the shifted plasmonic-resonance peak 622 associated with second configuration 620 of FIG. 6A. The plasmonic-resonance peak 612 associated with first configuration 610 has its maximum value at wavelength 614 that defines an amplitude 616 of the plasmonic-resonance peak 612. The shifted plasmonic-resonance peak 622 associated with second configuration 620 has its maximum value at wavelength 624 that defines the amplitude 626 of the shifted plasmonic-resonance peak 622. In accordance with one example of the present invention, the plasmonic-resonance peak 612 associated with luminescence from the analyte molecule 220-1 is shifted towards longer wavelengths of the shifted plasmonic-resonance peak 622. As shown in FIG. 6B, a magnitude of a shift 628 of the plasmonic-resonance peak 612 is indicated by the horizontal arrow. As shown in FIG. 6B, the amplitude 626 of the shifted plasmonic-resonance peak 622 is increased above the amplitude 616 of the plasmonic-resonance peak 612. Although the amplitude increase is shown as at least four times upon shifting, this is by way of example without limitation thereto, as the intensity scale may be logarithmic. On the other hand, in another example of the present invention, the plasmonic-resonance peak 612 associated with luminescence from the analyte molecule 220-1 may be shifted towards shorter wavelengths of a shifted plasmonic-resonance peak (not shown).

With further reference to FIGS. 6A and 6B, in accordance with one or more examples of the present invention, the basic principle of operation of the metallic-nanofinger device 101 for chemical sensing is depicted. In accordance with one or more examples of the present invention, a pair, alternatively, a threesome, or foursome, of metallic nanofingers is initially prepared to be well separated, for example, with a separation somewhat greater than about 10 nm. The metallic cap, for example, metallic cap 120-1B, may be composed of a material such as gold or silver as previously described in the discussion of FIGS. 5A-5C, such that the metallic cap will have a distinct plasmonic-resonance peak 612 as shown in FIG. 6B. Then under certain conditions, as previously described in the discussion of FIG. 3, such a pair, alternatively, a threesome, or foursome, of metallic nanofingers, for example, metallic nanofingers 120-1 and 120-2, will close the gap that initially lies between them, as previously shown in FIGS. 3, 4 and 6A. As a result, the plasmonic-resonance peak 612 of the structure will shift as indicated by the shift 628. The shift 628 is usually a red-shift, to longer wavelengths, due to the plasmonic coupling between two or more metallic caps, also referred to as "nanotips," of metallic nanofingers disposed in close proximity, less than about 5 nm, to one another. The shift 628 of the plasmonic-resonance peak 612 can be measured by a simple optical setup, such as a colorimeter or spectrometer, with a broadband illumination, for example, with white light from a light-emitting diode (LED). The optical components along with the metallic nanofingers can be integrated together to offer a miniaturized sensor, or even a lab-on-chip, as is subsequently described.

Figure 6C:
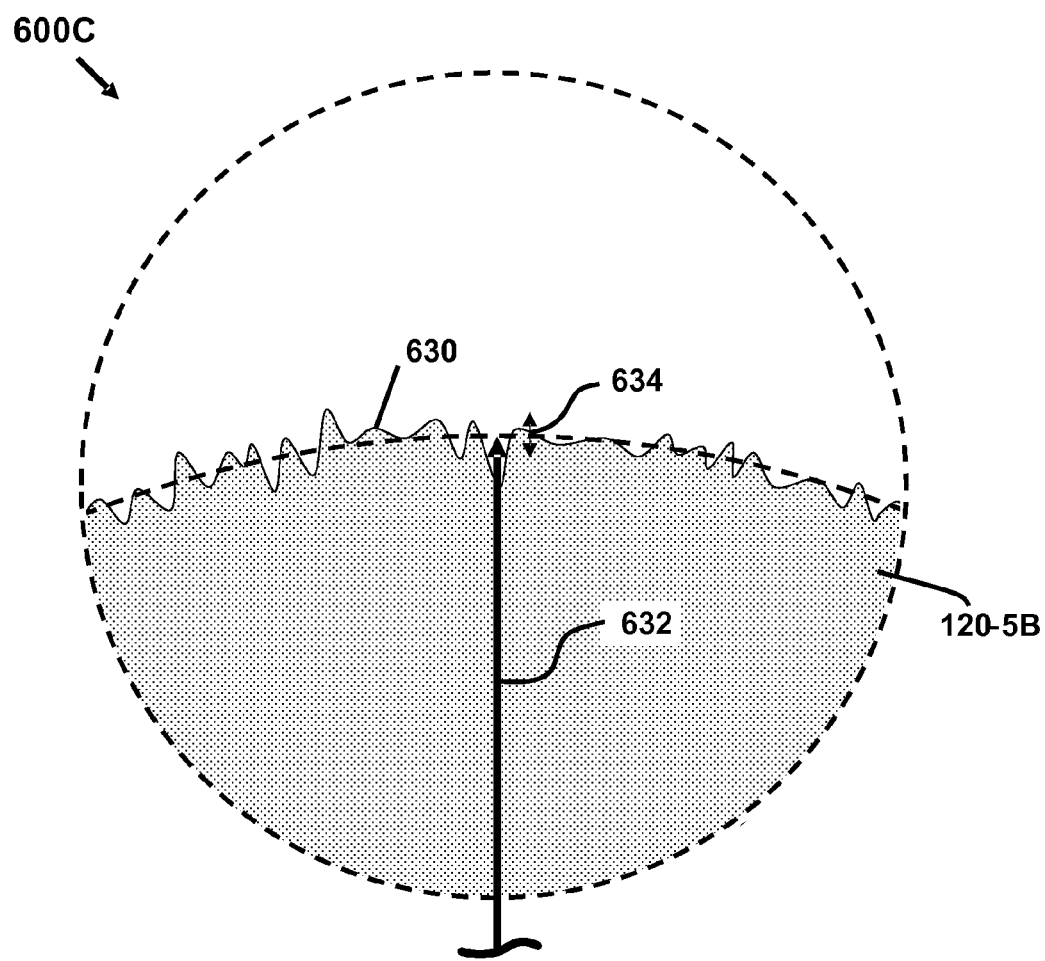
FIG. 6C is a cross-sectional elevation view, from the circle 6C of FIG. 6A, of the morphology of a metallic cap of a nanofinger of the metallic-nanofinger device for chemical sensing that is to enhance the amplitude of the plasmonic-resonance peak with shifting to longer wavelengths shown in FIG. 6B, in accordance with one or more examples of the present invention.

With reference now to FIG. 6C, in accordance with one or more examples of the present invention, a cross-sectional elevation view 600C, from the circle 6C of FIG. 6A, of the morphology of the metallic cap 120-1B of the nanofinger 120-1 of the metallic-nanofinger device 101 for chemical sensing is shown. The morphology of the metallic cap 120-1B is to enhance the amplitude of the plasmonic-resonance peak 612 with shifting to longer wavelengths as shown in FIG. 6B. The morphology of the metallic cap 120-1B as measured by a roughness average 634 of a surface roughness of the metallic cap 120-1B is such that the roughness average 634 is less than about 5 nm. In one example of the present invention, the morphology of the metallic cap 120-1B may be substantially spherical, without limitation thereto; and, the shape parameter includes the average radius 632 of the metallic cap 120-1B. In another example of the present invention, the morphology of the metallic cap 120-1B may be truncated substantially spherical such that the morphology of the cap 120-1B of the nanofinger 120-1 is similar to that of the head of a match stick, without limitation thereto; and, the shape parameter includes an average radius, similar to average radius 632, to the spherical surface portion of the metallic cap 120-1B that has truncated substantially spherical morphology. As used herein, a truncated spherical morphology may also include: a hemispherical morphology, also called a semispherical morphology; a spherical-cap morphology such that the height of the spherical cap is less than a radius of the respective sphere corresponding to the spherical cap by geometrical construction; and, a sphere-less-a-spherical-cap morphology such that the portion of the sphere with a spherical-cap portion removed corresponds to the shape of the truncated spherical morphology. On the other hand, in other examples of the present invention, the morphology of the metallic cap 120-1B may be that of an oblate ellipsoid as shown in FIGS. 1-5, or one of the other shapes previously described. In the case of an oblate ellipsoid, the shape parameter may be taken as the major axis of the oblate ellipsoid; alternatively, other shape parameters may be chosen suitable to a particular shape of a metallic cap.

With further reference to FIG. 6C, in one example of the present invention, the morphology of the metallic cap 120-1B as measured by the shape parameter of the metallic cap 120-1B is such that the shape parameter varies from metallic cap to metallic cap of respective metallic nanofingers by no more than between plus 5 nm to minus 5 nm from an average value of the shape parameter; for example, the average radius 632 of a substantially spherical metallic cap might vary from metallic cap to metallic cap of respective metallic nanofingers by no more than between plus 10 nm to minus 10 nm. Similarly, the average radius, similar to average radius 632, of a truncated substantially spherical metallic cap might vary from metallic cap to metallic cap of respective metallic nanofingers by no more than between plus 10 nm to minus 10 nm. In another example of the present invention, the morphology of the metallic cap 120-1B as measured by a shape parameter of the metallic cap 120-1B is such that the shape parameter varies from metallic cap to metallic cap of respective metallic nanofingers by no more than between plus 10 nm to minus 10 nm from an average value of the shape parameter.

Figure 6D:
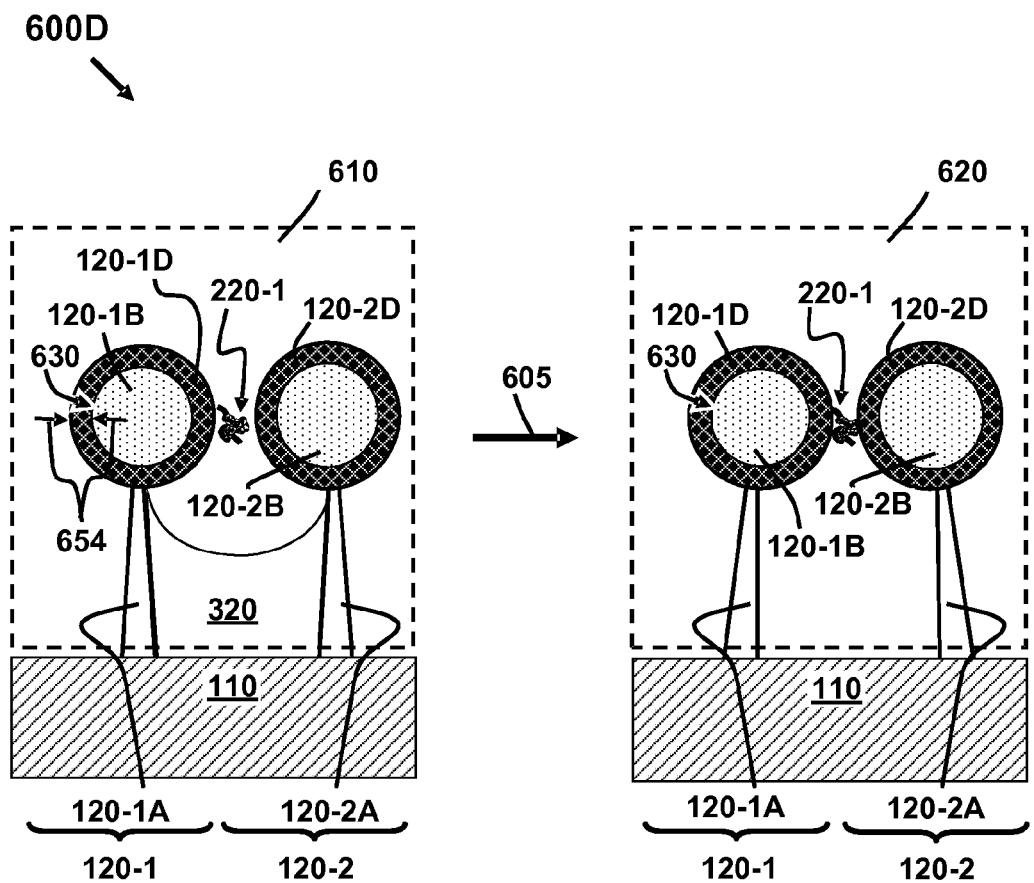
FIG. 6D is a cross-sectional elevation view, similar to that of FIG. 6A, of the metallic-nanofinger device for chemical sensing having nanofingers with coatings disposed on substantially spherical metallic caps that schematically shows a change in configuration of the nanofingers upon self-arranging into a close-packed configuration, in accordance with one or more examples of the present invention.

With reference now to FIG. 6D, in accordance with other examples of the present invention, another cross-sectional elevation view 600D, similar to that of FIG. 6A, of the metallic-nanofinger device 101 for chemical sensing is shown. FIG. 6D schematically illustrates a change in configuration of the nanofingers 120-1 and 120-2, which include coatings 120-1D and 120-2D disposed on respective metallic caps 120-1B and 120-2B, upon self-arranging into a close-packed configurations. FIG. 6D shows a first configuration 610 of nanofingers 120-1 and 120-2 after wetting with the liquid 212 and upon formation of liquid pool 320. FIG. 6D also shows a second configuration 620 of nanofingers 120-1 and 120-2 after removal of the liquid 212 and self-arranging of nanofingers 120-1 and 120-2 into a close-packed configuration. The metallic-nanofinger device 101 includes the substrate 110 and the plurality 120 of nanofingers. The nanofinger 120-1 includes the flexible column 120-1A, the metallic cap 120-1B coupled to an apex 120-1C (previously described in FIGS. 5B and 5C) of the flexible column 120-1A, and a coating 120-1D encapsulating the metallic cap 120-1B. In addition, as shown in FIG. 6D, other nanofingers in the plurality 120 may also include a coating, for example, coating 120-2D, encapsulating a respective metallic cap, for example, metallic cap 120-2B. At least the nanofinger 120-1 and the second nanofinger 120-2 are to self-arrange into a close-packed configuration with at least one analyte molecule 220-1 disposed between at least the metallic cap 120-1B and a second metallic cap 120-2B of respective nanofinger 120-1 and second nanofinger 120-2. However, in addition, in accordance with another example of the present invention, the coating 120-1D is to develop a response upon exposure to the liquid 212 (see FIG. 2). The coating 120-1D has a thickness 654 of a few nanometers. Moreover, as previously described in the discussions of FIGS. 6A-6C, the morphology of the metallic cap 120-1B may also be to generate the shifted plasmonic-resonance peak 622 with enhanced amplitude 626 associated with amplified luminescence from the analyte molecule 220-1. Other elements shown in FIG. 6D are as previously described in the discussion of FIG. 6A.

With further reference to FIG. 6D, in accordance with one example of the present invention, the liquid 212 may include a solute; the solute includes the analyte molecule 220-1; and, the coating 120-1D has an affinity to react with the analyte molecule 220-1. In one example of the present invention, the liquid 212 does not include a solvent of the coating 120-1D; and, the liquid 212 does not dissolve the coating 120-1D. In another example of the present invention, the liquid 212 further includes a solute; the solute includes the analyte molecule 220-1; the coating 120-1D has an affinity to react with the analyte molecule 220-1; and, the analyte molecule 220-1 is left bound to the coating 120-1D encapsulating the metallic cap 120-1B. In another example of the present invention, the coating 120-1D may include a substance selected from the group consisting of polymethylmethacrylate (PMMA), a compound soluble in a solvent, a compound insoluble in a solvent, at least one antibody, and at least one antigen, at least one deoxyribonucleic acid segment, at least one ribonucleic acid segment, at least one protein, at least one protein segment, substances to develop a response upon exposure to the liquid 212, and substances to develop a response upon exposure to an analyte molecule 220-1 in the liquid 212. An example of the present invention in which the coating of the metallic cap of a metallic nanofinger, for example, coating 120-1D of the metallic cap 120-1B of metallic nanofinger 120-1, includes a compound soluble in a solvent is next described.

Figure 6E:
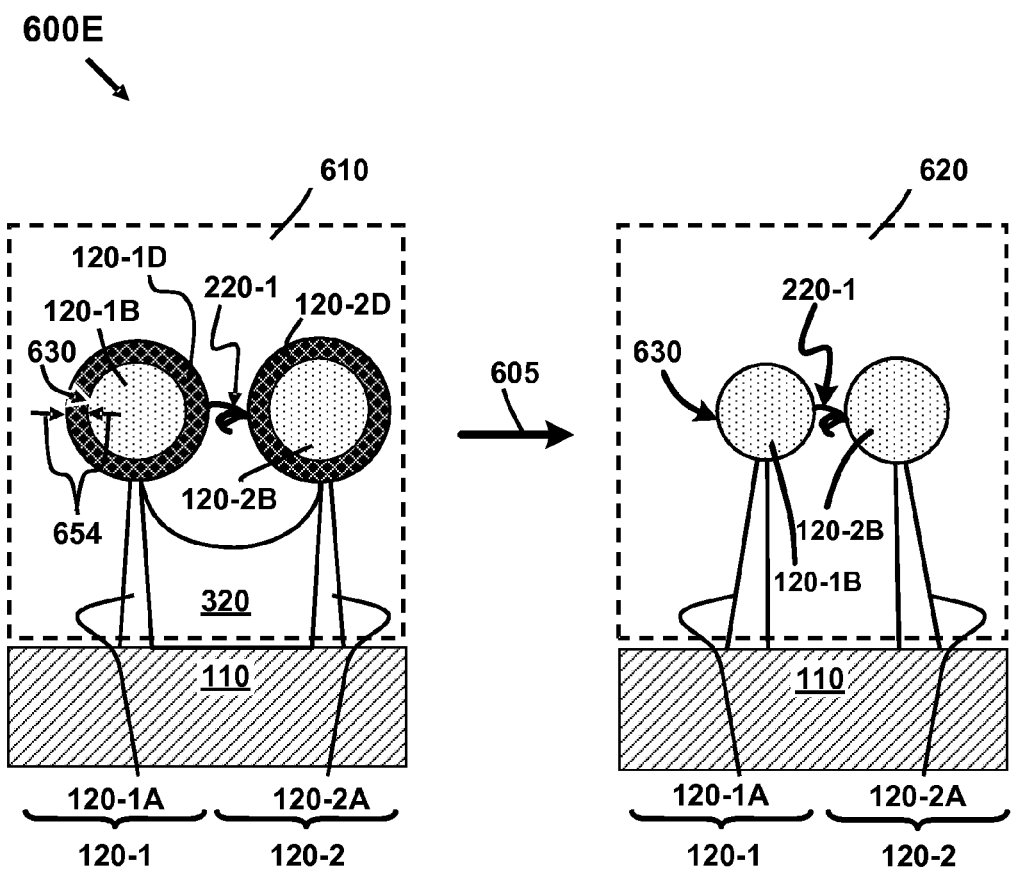
FIG. 6E is a cross-sectional elevation view, similar to that of FIG. 6D, of the metallic-nanofinger device for chemical sensing having nanofingers with coatings that dissolve upon exposure to a liquid that schematically shows a change in configuration of the nanofingers upon self-arranging into a close-packed configuration attending the dissolution of the coatings, in accordance with one or more examples of the present invention.

With reference now to FIG. 6E, in accordance with other examples of the present invention, another cross-sectional elevation view 600E of the metallic-nanofinger device 101 for chemical sensing, similar to that of FIG. 6D, is shown. FIG. 6E schematically shows a change in configuration, from first configuration 610 to second configuration 620, of the nanofingers, which include the coating disposed on the metallic cap, for example, coating 120-1D on metallic cap 120-1B, that dissolves upon exposure to a liquid upon self-arranging into a close-packed configurations. In one example of the present invention, liquid 212 includes a solvent for the coating 120-1D; and, the solvent dissolves the coating 120-1D. In another example of the present invention, liquid 212 further may include a solute; the solute includes the analyte molecule 220-1; the coating 120-1D has an affinity to react with the analyte molecule 220-1; and, the analyte molecule 220-1 is left bound to the metallic cap 120-1B.

As previously described in the discussion of FIGS. 6D and 6E, in accordance with one or more examples of the present invention, chemical functionality is incorporated within the coating in order to provide chemical sensing capability for the metallic-nanofinger device 101; thus, making the metallic-nanofinger device 101 for chemical sensing a chemical sensor. In one example of the present invention, the plurality 120 of metallic nanofingers is coated with a material to maintain a separation, d, between two neighboring metallic nanofingers even when a pair, or more than two metallic nanofingers, come into contact with one another, for example, as occurs upon exposure to and subsequent purging the liquid 212 from the metallic-nanofinger device 101. For example, then upon exposure of the coating, for example, coating 120-1D, to analyte present in the liquid 212, a chemical reaction between the analyte present in the liquid 212 and the coating may result in removal of the coating, for example, coatings 120-1D and 120-2D, from the surfaces of metallic nanofingers, of which surface 630 of the metallic cap 120-1B is an example. Consequently, under microcapillary forces, the two neighboring metallic nanofingers, for example, metallic nanofingers 120-1 and 120-2, will self-close to shift the plasmonic resonance peak 612 to shifted plasmonic-resonance peak 622, as shown in FIG. 6C.

For example, with further reference to FIGS. 6D and 6E, in accordance with one example of the present invention, the substance of the coating, for example, coating 120-1D, may be PMMA; and, a solvent, or alternatively, a solute, in liquid 212 may be acetone. When the gold metallic cap of the metallic nanofinger, for example, metallic cap 120-1B of metallic nanofinger 120-1, is initially coated with a thin layer of PMMA or any other acetone soluble material, with exposure to the acetone, the PMMA coating will be dissolved away. As the surface dries out, microcapillary forces will draw the two metallic nanofingers, for example, metallic nanofingers 120-1 and 120-2, close to one another; and, a red-shifted plasmonic-resonance peak 622 will be observed upon illuminating the metallic-nanofinger device 101 with a source 910 of exciting electromagnetic radiation 915, as shown in FIG. 9. But, if the metallic-nanofinger device 101 is exposed instead to any of the following, water, ethanol, or isopropyl alcohol (IPA), as the primary constituent present in the liquid 212, the PMMA layer will not dissolve. As a result, the plasmonic-resonance peak 612 will not be red-shifted to the position of the shifted plasmonic-resonance peak 622, nor will the amplitude of the plasmonic-resonance peak be greatly enhanced as occurs upon shifting of the plasmonic-resonance peak, as depicted in FIG. 6B. The presence, or alternatively, the absence of the shifted plasmonic-resonance peak 622 upon exposure to and purging of the liquid 212 may then be used to test for constituents in the liquid that respectively dissolve, or do not dissolve, the coating, of which coatings 120-1D and 120-2D are examples, similar to the way a litmus test is used to test for the presence of acidity. Thus, in one example of the present invention, the metallic-nanofinger device 101 may be integrated with a platform 820 to provide a chemical-analysis device 801 (see FIG. 8) that is a test strip, similar to litmus paper, as is subsequently described in greater detail.

In another example, with further reference to FIGS. 6A-6E, in accordance with one or more examples of the present invention, the substance of the coating, for example, coating 120-1D, may include an antibody, such that only a specific antigen, for example, analyte molecule 220-1, can bind with the antibody of the coating with high specificity. Upon exposure of the metallic-nanofinger device 101 to the liquid 212 that is a solution containing antigen, as analyte molecules, antigen will bind to the antibody contained in the coating on the surface of a metallic nanofinger surface, of which surface 630 of the metallic cap 120-1B is an example. As a result the separation, d, of the neighboring metallic nanofingers, for example, metallic nanofingers 120-1 and 120-2, will be different from the case in which there is no antigen present in the liquid 212 after the liquid is removed from the metallic-nanofinger device 101. Therefore, in accordance with one or more examples of the present invention, the metallic-nanofinger device 101 can be used as sensor to do bio-analysis with high specificity. Since there is no need to do bio-labeling on the liquid 212 containing analyte sample, the metallic-nanofinger device 101 provides a label-free sensor. Thus, one or more examples of the present invention provide a technique that does not depend on fluorescence; and, the adverse effects of photobleaching, fluorescence quenching, half-life of the fluorophore, as well as an expensive optical setup, can be avoided. In accordance with examples of the present invention, the attachment of the antigen probe on the surface of the metallic cap of the metallic nanofinger can be provided by thiol-linker chemistry, which is well known in the art of protein micro-array and DNA micro-array technologies. Moreover, the inventors believe that existing antigen-antibody reactions employed in contemporary bio-assay art can potentially be implemented within the scope of examples of the present invention by using antibody-functionalized coatings, or alternatively, antigen-functionalized coatings, on metallic caps of the metallic-nanofinger device 101 for chemical sensing.

Figure 7A:
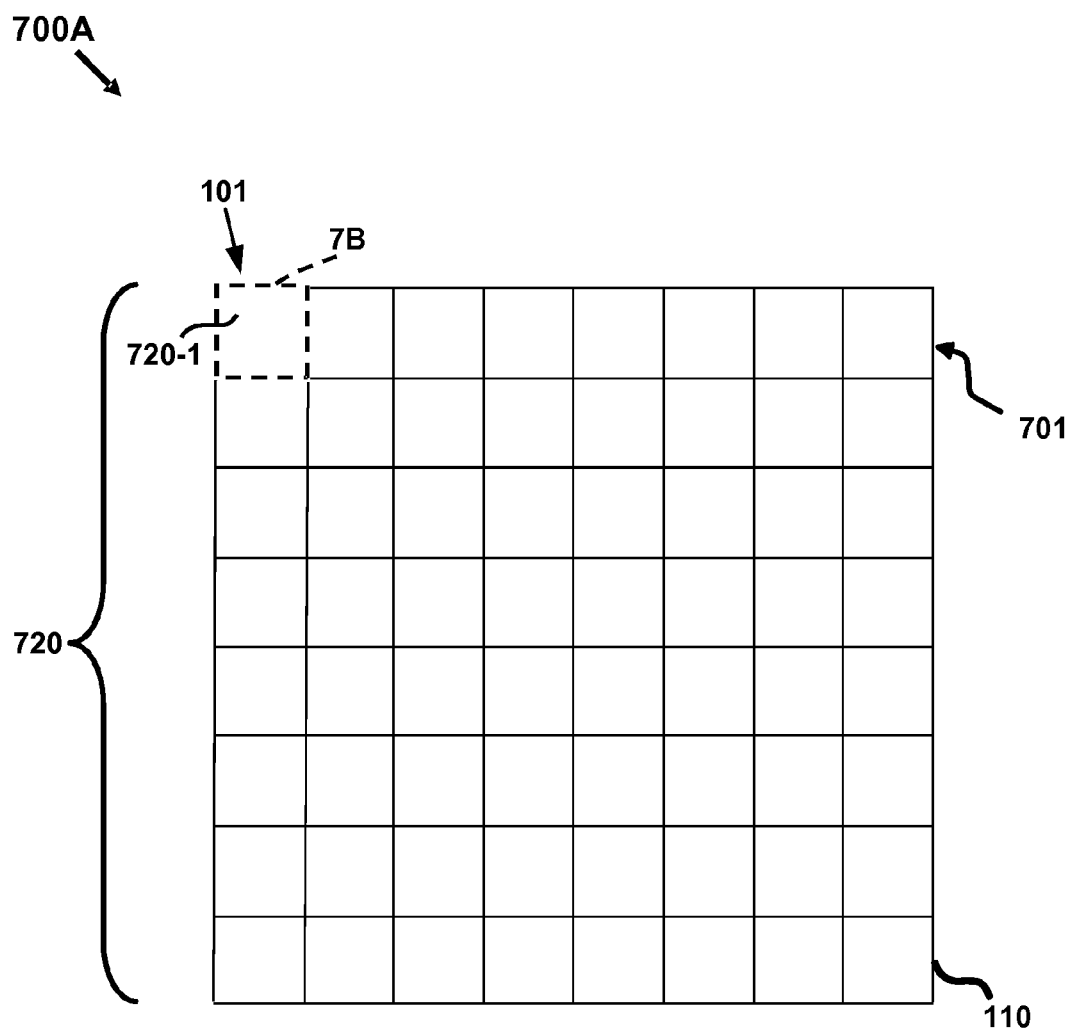
FIG. 7A is a plan view of a chemical-sensing chip including the metallic-nanofinger device for chemical sensing that schematically shows the arrangement of an array of patches included in the chemical-sensing chip, in accordance with one or more examples of the present invention.

With reference now to FIG. 7A and further reference to FIGS. 6A-6E, in accordance with one or more examples of the present invention, a plan view 700A is shown of a chemical-sensing chip 701 including the metallic-nanofinger device 101 for chemical sensing. FIG. 7A schematically shows the arrangement within the chemical-sensing chip 701 of an array 720 of patches, of which patch 720-1 is an example. The chemical-sensing chip 701 includes the metallic-nanofinger device 101. The metallic-nanofinger device 101 includes the substrate 110, and the array 720 of patches. The patch 720-1 of the array 720 includes a plurality 120 of nanofingers. The nanofinger 120-1 includes the flexible column 120-1A, the metallic cap 120-1B coupled to an apex 120-1C (previously described in FIGS. 5B and 5C) of the flexible column 120-1A, and the coating 120-1D encapsulating the metallic cap 120-1B. At least the nanofinger 120-1 and the second nanofinger 120-2 are to self-arrange into a close-packed configuration with at least one analyte molecule 220-1 disposed between at least the metallic cap 120-1B and a second metallic cap 120-2B of respective nanofinger 120-1 and second nanofinger 120-2. In accordance with one example of the present invention, the morphology of the metallic cap 120-1B may be to generate the shifted plasmonic-resonance peak 622 with enhanced amplitude 626 associated with amplified luminescence from the analyte molecule 220-1. In addition, in accordance with another example of the present invention, the coating 120-1D of the metallic cap 120-1B in the patch 720-1 may be functionalized with certain molecular probe species to develop a specific response upon exposure to certain targets in the liquid 212 (see FIG. 2), which includes the targets in an analyte solution. In accordance with another example of the present invention, chemical-sensing chip 701 can also be fabricated such that each patch location can be specifically functionalized with certain molecular probe species, which can respond specifically to certain targets in a complex analyte solution. Thus, in accordance with examples of the present invention, the chemical-sensing chip 701 may provide a highly parallel detection device through utilization of such an array 720 of specifically functionalized patches. A square portion 7B of the chemical-sensing chip 701 outlined with dashed lines identifies one such patch 720-1 of the array 720 of patches, which is next described.

Figure 7B:
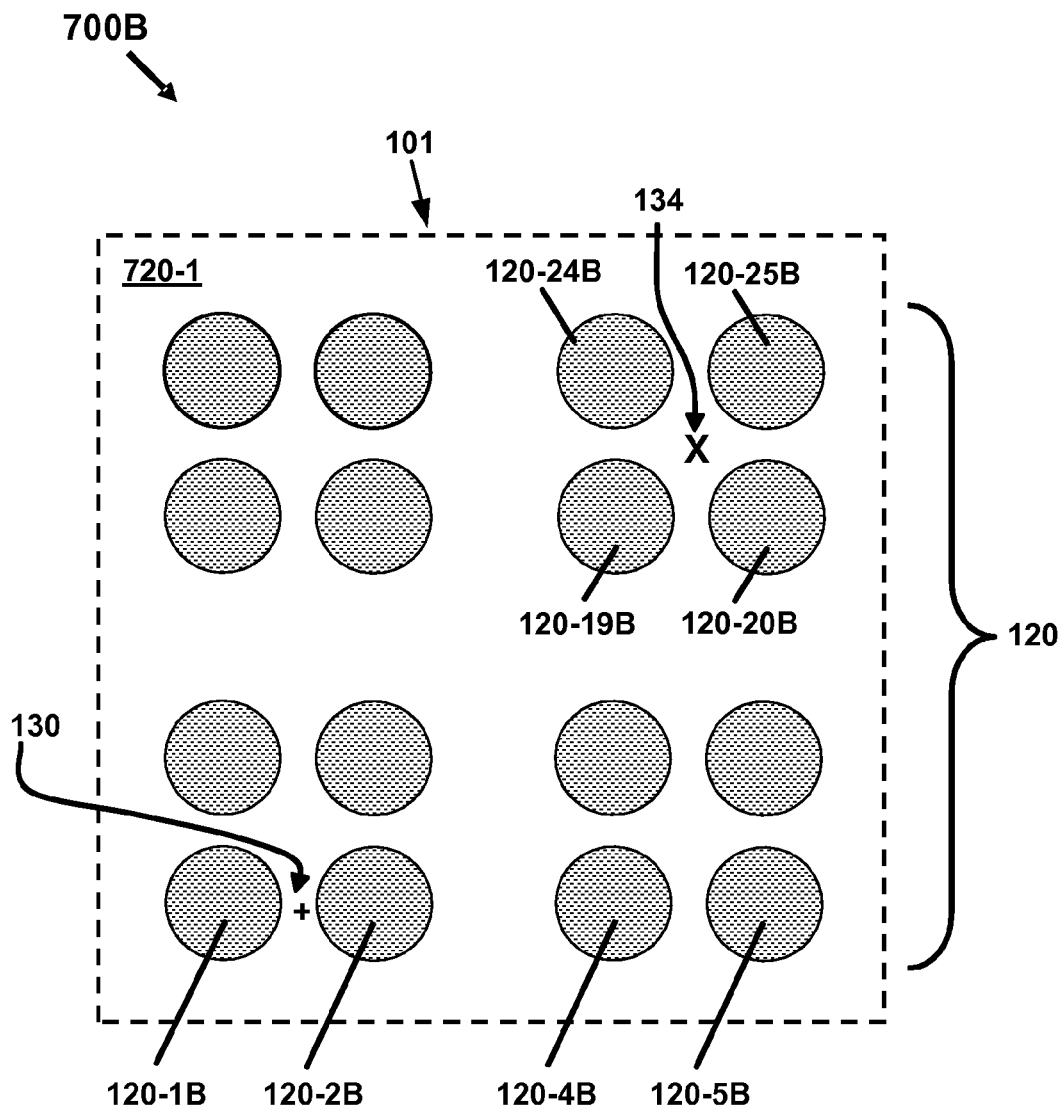
FIG. 7B is a plan view of a patch, from the square portion 7B of FIG. 7A, in the array of patches that schematically shows the arrangement of the metallic caps disposed on a plurality of nanofingers in the patch, in accordance with one or more examples of the present invention.

With reference now to FIG. 7B, in accordance with one or more examples of the present invention, a plan view 700B is shown of the patch 720-1 corresponding to the square portion 7B of FIG. 7A. FIG. 7B schematically shows a plurality 120 of nanofingers in the patch 720-1 in the array 720 of patches. As shown in FIG. 7B, the locations of the nanofingers is indicated by the location of their respective metallic caps. For example, the metallic caps 120-1B and 120-2B correspond to the location of nanofingers 120-1 and 120-2; similarly, the metallic caps 120-19B, 120-20B, 120-24B and 120-25B correspond to the location of nanofingers 120-19, 120-20, 120-24 and 120-25. As shown in FIG. 7B, "streets" have been fabricated in the array 120 of nanofingers by the removal of a row and/or a column of nanofingers from the array 120. As previously described in PCT Patent Application, Serial Number PCT/US10/31809 by Zhiyong Li, et al., filed on Apr. 20, 2010, entitled "A SELF-ARRANGING, LUMINESCENCE-ENHANCEMENT DEVICE FOR SURFACE-ENHANCED LUMINESCENCE," the streets facilitate the rearrangement of local clusters of the nanofingers due the action of capillary forces described above, for example, in the discussion of FIGS. 3, 6A, 6D and 6E. Two interstices are also show in FIG. 7B: small interstice 130 corresponding to a rearrangement between the metallic caps 120-1B and 120-2B of respective nanofingers 120-1 and 120-2 for the capture of an analyte molecule 220-1, as previously described in the discussion of FIGS. 3, 6A, 6D and 6E; and, large interstice 134, similar to the large interstice 132 described in the discussion of FIGS. 1 and 4, located between the four the metallic caps 120-19B, 120-20B, 120-24B and 120-25B of respective nanofingers 120-19, 120-20, 120-24 and 120-25 for the capture of an analyte molecule, similar to analyte molecule 410, as previously described in the discussion of FIG. 4.

Figure 8:
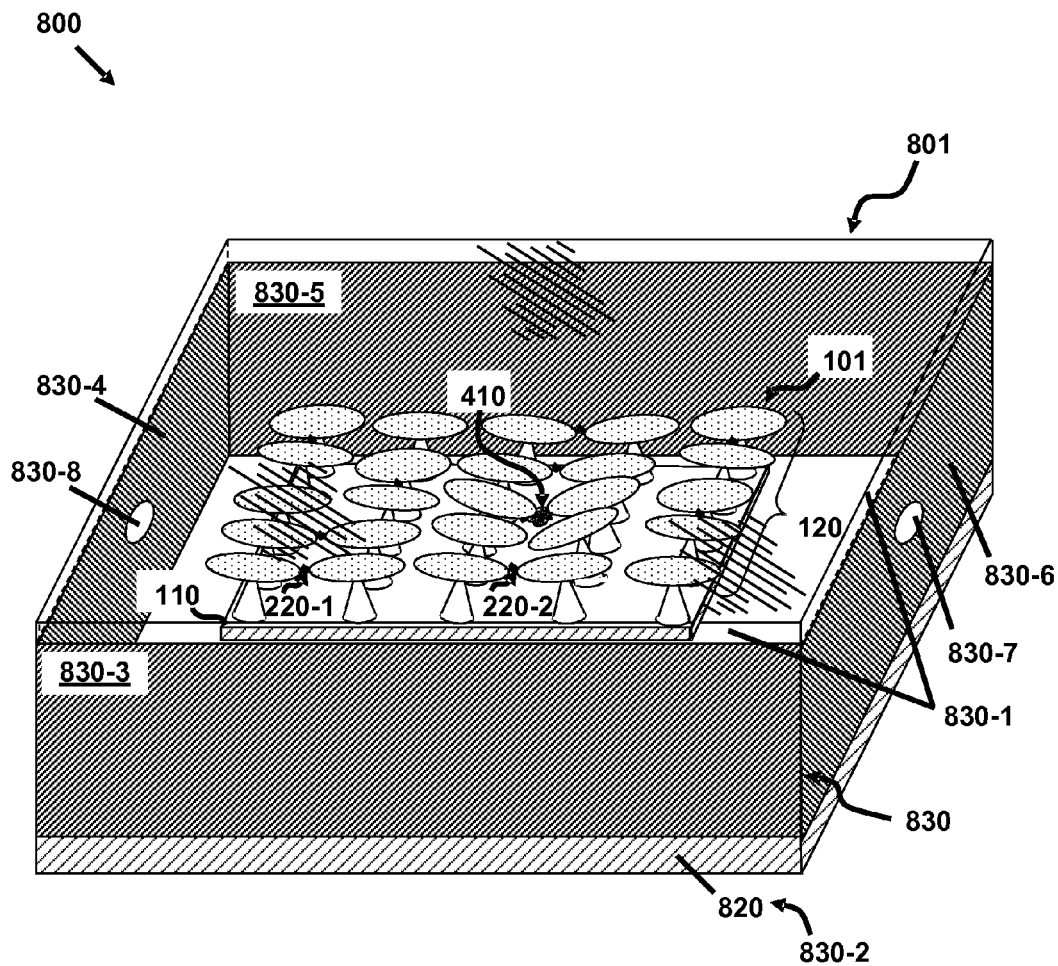
FIG. 8 is a perspective view of a chemical-analysis device integrated with the metallic-nanofinger device for chemical sensing, in accordance with one or more examples of the present invention.
Figure 9:
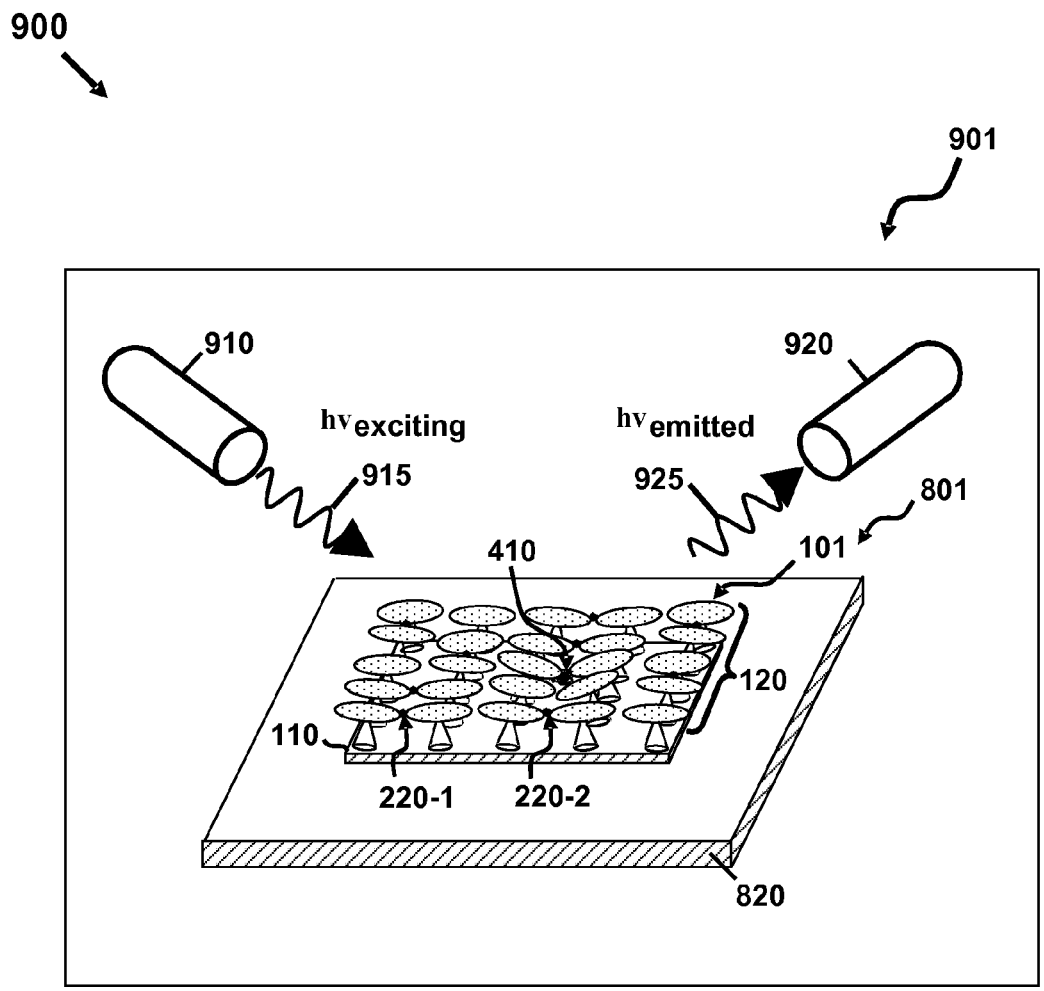
FIG. 9 is a perspective view of a chemical-analysis apparatus including the chemical-analysis device integrated with the metallic-nanofinger device for chemical sensing, in accordance with one or more examples of the present invention.

With reference now to FIG. 8 and further reference to FIGS. 1-6E, in accordance with one or more examples of the present invention, a perspective view 800 is shown of a chemical-analysis device 801 integrated with the metallic-nanofinger device 101 for chemical sensing. The chemical-analysis device 801 integrated with a metallic-nanofinger device 101 includes the metallic-nanofinger device 101, and a platform 820 with which the metallic-nanofinger device 101 is coupled. The metallic-nanofinger device 101 includes the examples previously described above, as these examples may be incorporated within the environment of the chemical-analysis device 801 being within the spirit and scope of examples of the present invention. The metallic-nanofinger device 101 is to produce a change in optical response from the metallic-nanofinger device 101 upon exposing the chemical-analysis device 801 to the liquid 212, and purging the chemical-analysis device 801 of the liquid 212. The chemical-analysis device 801 may further include an enclosure 830 encapsulating the metallic-nanofinger device 101 and to confine the analyte molecule 220-1 within the enclosure 830. In one example of the present invention, the enclosure 830 includes a micro-fluidic channel to transport the liquid 212 to and from the metallic-nanofinger device 101 disposed within a portion of the micro-fluidic channel. In another example of the present invention, the enclosure 830 of the chemical-analysis device 801 may include a combined micro-fluidic channel and waveguide. The combined micro-fluidic channel and waveguide is configured both to transport the liquid 212 to and from the metallic-nanofinger device 101 contained within a portion of the micro-fluidic channel, and to conduct exciting electromagnetic radiation 915 (see FIG. 9) to the metallic-nanofinger device 101 and emitted electromagnetic radiation 925 (see FIG. 9) away from the metallic-nanofinger device 101.

With further reference to FIG. 8 and FIGS. 1-7A, in accordance with one or more examples of the present invention, the enclosure 830 of the chemical-analysis device 801 may include: an enclosure cover 830-1, an enclosure base 830-2, enclosure sidewalls 830-3, 830-4, 830-5, 830-6 attached to the enclosure cover 830-1 and attached to the enclosure base 830-2, an enclosure inlet 830-7 to admit the liquid 212 into the enclosure, and an enclosure outlet 830-8 to remove the liquid 212 from the enclosure 830. By way of example, the enclosure 830 has been shown in FIG. 8 as a box-like structure such that the enclosure base 830-2 includes the platform 820. However, in another example of the present invention, the enclosure base 830-2 may be separate from the platform 820; for example, within the spirit and scope of examples of the present invention, the chemical-analysis device 801 including the metallic-nanofinger device 101 and the platform 820 may include an enclosure having a cylindrical, or other alternative shape such that the metallic-nanofinger device 101 and the platform 820 are disposed within an enclosure having its own enclosure base or base-like portion. Moreover, within the spirit and scope of examples of the present invention, although the enclosure cover 830-1, the enclosure base 830-2 and the enclosure sidewalls 830-3, 830-4, 830-5, 830-6 are shown as essentially planar structures, the enclosure cover 830-1, the enclosure base 830-2 and the enclosure sidewalls 830-3, 830-4, 830-5, 830-6 may have shapes other than shown in FIG. 8, without limitation thereto. Similarly, although, by way of example, the enclosure inlet 830-7 and the enclosure outlet 830-8 are shown in FIG. 8 as orifices in the respective enclosure sidewalls 830-4 and 830-6, the enclosure inlet 830-7 and the enclosure outlet 830-8 may include other structures such as tubes, channels or ducts, which are within the spirit and scope of examples of the present invention. Moreover, within the spirit and scope of examples of the present invention, a shape and geometrical configuration of the enclosure 830, other than depicted in FIG. 8 by way of example, may be provided by microfabrication techniques.

With further reference to FIG. 8 and FIGS. 1-7A, in accordance with one or more examples of the present invention, any of the enclosure cover 830-1, the enclosure base 830-2, the enclosure sidewalls 830-3, 830-4, 830-5, 830-6, the platform 820, and the substrate may be transparent to exciting electromagnetic radiation 915 (see FIG. 9) that may be used to excite the analyte molecule 220-1, and may be transparent to emitted electromagnetic radiation 925 (see FIG. 9) that may be emitted from the analyte molecule 220-1 in response to the exciting electromagnetic radiation 915. The plurality 120 of nanofingers coupled with the substrate 110 of the metallic-nanofinger device 101 may further include the coating 120-1D encapsulating the metallic cap 120-1B, where the coating 120-1D is to develop a response upon exposure to the liquid 212. The chemical-analysis device 801 may further include the chemical-sensing chip 701 that includes the metallic-nanofinger device 101; the metallic-nanofinger device 101 may further include the array 720 of patches, where a patch 720-1 of the array 720 includes the plurality 120 of nanofingers coupled with the substrate 110; and, the coating 120-1D of the metallic cap 120-1B in the patch 720-1 may be functionalized with a certain probe molecule to develop a specific response upon exposure to certain targets in the liquid 212 including targets in a complex analyte solution. Each patch 720-1 of the array 720 of patches may further include a micro-fluidic channel configured both to confine the analyte molecule 220-1 within the micro-fluidic channel, and to transport the liquid 212 to and from the metallic-nanofinger device 101 disposed within a portion of the micro-fluidic channel. Thus, in accordance with examples of the present invention, the array 720 of patches may be configured as a lab-on-chip, which is next described in greater detail.

For example, with further reference to FIG. 8 and FIGS. 1-7A, in accordance with one or more examples of the present invention, the metallic-nanofinger device 101 of chemical-analysis device 801 may be integrated inside the micro-fluidic channel, so that a liquid sample, for example, liquid 212, as shown in FIG. 2, can be introduced to the metallic-nanofinger device 101 in small volume to allow easy implementation as the lab-on-chip. For example, in one or more examples of the present invention, the following operations may be preformed: liquid 212 may be introduced from the enclosure inlet 830-8; sufficient interaction time may then be provided for interaction of the liquid 212 with the metallic-nanofinger device 101; a gas, for example, air, may be blown through the enclosure, for example, the micro-fluidic channel, to purge the metallic-nanofinger device 101 of the liquid 212 and to dry the metallic-nanofingers of the metallic-nanofinger device 101; and, sufficient time may then be provided for the metallic-nanofingers to close under microcapillary forces. For example, in another example of the present invention, either one or both of the top and the bottom of the micro-fluidic channel may be configured as an optical window that is transparent allowing optical measurements to be made from chemical-analysis device 801 both before and after the interaction with the liquid 212. Alternatively, in another example of the present invention, illumination and measurement can also be done through two enclosure sidewalls, for example, enclosure sidewalls 830-3 and 830-5, of a micro-fluidic channel that provides the enclosure 830. For example, in another example of the present invention, the micro-fluidic channel itself may be a waveguide, for example, a metallic hollow waveguide, or a dielectric hollow waveguide, which can be used for illumination of the chemical-analysis device 801 and for detection of surface-enhanced luminescence from the chemical-analysis device 801. Moreover, in another example of the present invention, in the case of a chemical-analysis device 801 including a chemical-sensing chip 701, individual patches of the chemical-sensing chip 701 may be included in microfluidic channels daisy-chained together; the chemical-analysis device 801 including the chemical-sensing chip 701 may be configured such that the liquid 212 may pass from one patch to the next for analysis for the presence of specific analyte species that the nanofingers of each patch are functionalized to detect with functionalized coatings, as previously described, that are sensitive to specific analyte species.

Alternatively, in another example of the present invention, the chemical-analysis device 801 may further include a test strip. Examples of the present invention implemented as a test strip might be used in a fashion similar to litmus paper such that a change in reflectivity, light scattering, and fluorescence due to surface-enhanced reflectivity, surface-enhanced light scattering, and surface-enhanced fluorescence, respectively, may indicate with specificity the presence of a specific analyte molecule 220-1.

With reference now to FIG. 9, in accordance with one or more examples of the present invention, a perspective view 900 is shown of a chemical-analysis apparatus 901 including the chemical-analysis device 801 integrated with the metallic-nanofinger device 101 for chemical sensing. The chemical-analysis apparatus 901 includes the chemical-analysis device 801 integrated with the metallic-nanofinger device 101, a source 910 of exciting electromagnetic radiation 915 to excite the analyte molecule 220-1 captured by the chemical-analysis device 801, and a detector 920 to detect emitted electromagnetic radiation 925 that may be emitted from the analyte molecule 220-1 in response to the exciting electromagnetic radiation 915. The chemical-analysis apparatus 901 may also include a dispersion unit (not shown), such as a diffraction grating and slit interposed between the chemical-analysis device 801 and the detector 920; for such a spectroscopic configuration including a dispersion unit, the chemical-analysis apparatus 901 may selectively disperse the emitted electromagnetic radiation 925 as a function of wavelength. Alternatively, in other examples of the present invention, the chemical-analysis apparatus 901 might not be configured as a spectrometer with a dispersion unit, but as, for example, a reflectometer, without limitation thereto. The chemical-analysis device 801 includes the examples previously described above, as these examples may be incorporated within the environment of the chemical-analysis apparatus 901 being within the spirit and scope of examples of the present invention.

With further reference to FIG. 9 and further reference to FIGS. 1-8, in accordance with other examples of the present invention, an example configuration is shown for SERS, without limitation thereto, of analyte molecules disposed between the metallic caps of the metallic-nanofinger device 101 for chemical sensing. In accordance with one or more examples of the present invention, chemical-analysis device 801 may be selected from the group consisting of a mirror, a grating, a wave-guide, a microfluidic channel, a cuvette and an analytical cell any of which may be disposed in the chemical-analysis apparatus 901. In accordance with one or more examples of the present invention, the chemical-analysis apparatus 901 may include a spectrometer, for example, a Raman spectrometer, without limitation thereto. Thus, in accordance with one or more examples of the present invention, the chemical-analysis apparatus 901 may include, more generally, an instrument selected from the group consisting of a colorimeter, a reflectometer, a spectrometer, a spectrophotometer, a Raman spectrometer, an optical microscope, and an instrument to accept the chemical-analysis device 801 for optical analysis and/or spectroscopic analysis.

In another example, with further reference to FIGS. 1-9, in accordance examples of the present invention, one configuration of the chemical-analysis apparatus 901 includes a spectrometer to accept the chemical-analysis device 801 for performing spectroscopy, for example, SERS, of at least one molecule, for example, analyte molecule 220-1, analyte molecule 220-2, or analyte molecule 410. The spectrometer includes a source 910 of exciting electromagnetic radiation 915 that is used to excite at least one molecule, for example, analyte molecule 410. The source 910 of exciting electromagnetic radiation 915 may be a laser, without limitation thereto. The energy of a photon of the exciting electromagnetic radiation 915 is given by Planck's constant times the frequency of the laser source, given by: $h\nu_{laser}$. In addition, the spectrometer includes a dispersion unit (not shown) and a detector 920 that are used to analyze and detect emitted electromagnetic radiation 925. The emitted electromagnetic radiation 925 emerges from the analyte molecule 410 in response to the source 910 that includes an exciting laser. For example, in the case of SERS, the energy of a photon of the emitted electromagnetic radiation 925 from the analyte molecule 410 is given by Planck's constant, h, times the frequency of the molecular source, $\nu_{SERS}$, given by: $h\nu_{SERS} = h\nu_o \pm h\Delta$, where $\nu_o$ is the frequency of the incident laser field and $\Delta$ the Raman shift. Because of the interaction with surface plasmons excited in the plurality of metallic caps, for example, metallic caps 120-1B and 120-2B, metallic caps 120-3B and 120-4B, and metallic caps 120-8B, 120-9B, 120-13B and 120-14B, of the plurality of nanofingers, the magnitude of the local electric field $E_{molecule}$, at a molecule for example, analyte molecule 220-1, analyte molecule 220-2, or analyte molecule 410, respectively, is enhanced compared to the incident field $E_o$.

With further reference to FIGS. 1-9, in accordance with one or more examples of the present invention, the composition of the metallic cap is such that the surface plasmons excited in the metallic cap are within the wavelength ranges of the exciting electromagnetic radiation 915 and the electromagnetic radiation emitted from the analyte molecule 410; these wavelength ranges may extend from the near ultraviolet to the near infrared. Thus, in accordance with one or more examples of the present invention, the plurality of metallic caps may be composed of a noble metal constituent; or alternatively, the plurality of metallic caps may be composed of a constituent selected from the group of constituents consisting of copper, silver and gold. In accordance with an example of the present invention, the signal associated with the emitted electromagnetic radiation 925 is amplified by increasing the number of metallic caps in proximity to which a molecule is disposed. Examples of the present invention increase the number of metallic caps, for example, metallic caps 120-8B, 120-9B, 120-13B and 120-14B, in proximity to a molecule, for example, analyte molecule 410, by employing the plurality 120 of nanofingers including the plurality 510 (see FIG. 5B) of flexible columns upon which the plurality 530 (see FIG. 5C) of metallic caps are disposed. Thus, in accordance with one or more examples of the present invention, due to the increased number of metallic caps, an increase in the excitation of surface plasmons in proximity to the analyte molecule 410 is expected to enhance the signal from the analyte molecule 410 in SERS. Therefore, examples of the present invention provide a metallic-nanofinger device 101 that provides for surface-enhanced luminescence, for example, for SERS, without limitation thereto.

Figure 10A:
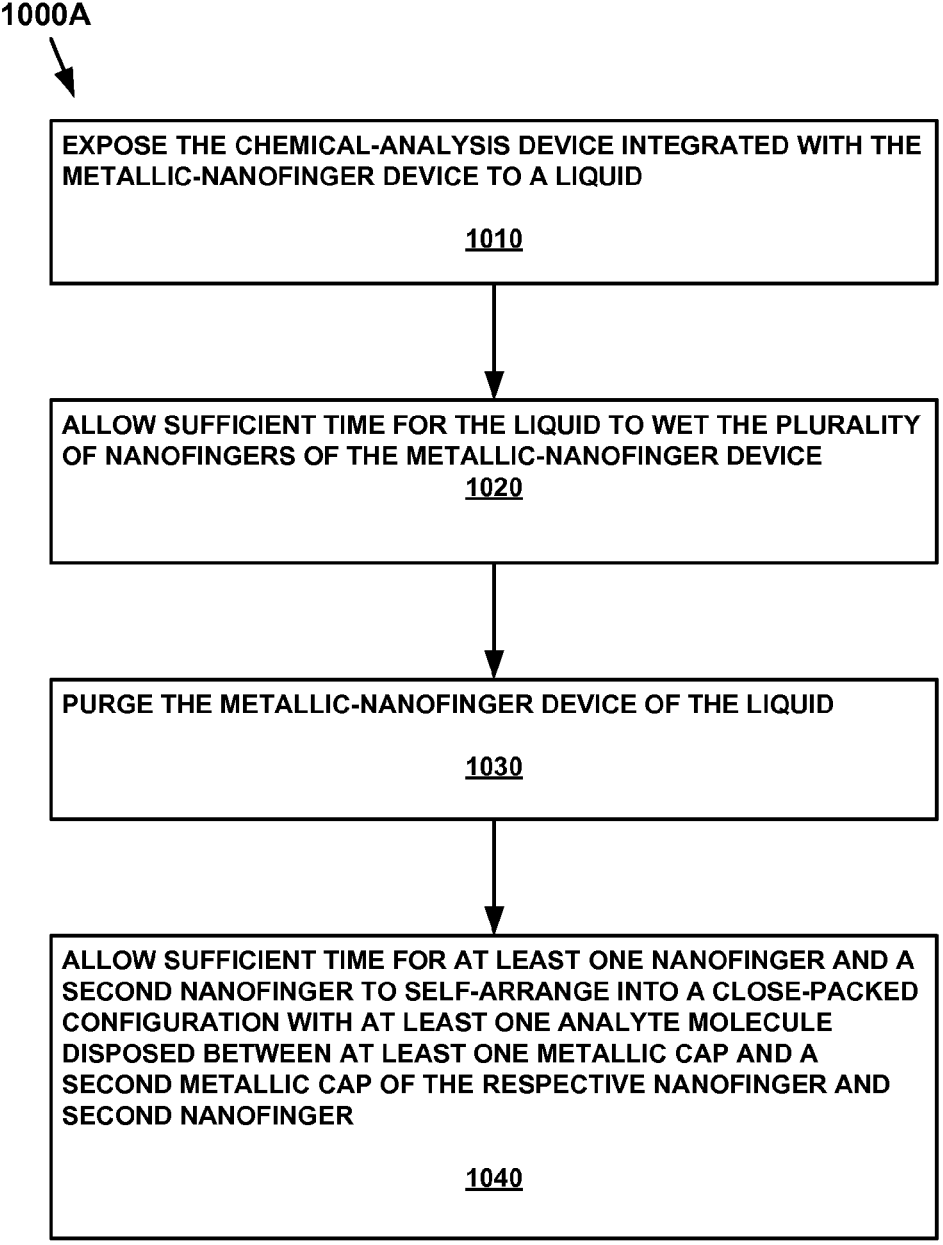
FIG. 10A is a flowchart of a method for using the chemical-analysis device integrated with the metallic-nanofinger device for chemical sensing, in accordance with one or more examples of the present invention.

With reference now to FIG. 10A, in accordance with one or more examples of the present invention, a flowchart 1000A is shown of a method for using a chemical-analysis device integrated with a metallic-nanofinger device for chemical sensing. The method for using the chemical-analysis device integrated with the metallic-nanofinger device for chemical sensing includes the following operations. At 1010 the chemical-analysis device integrated with the metallic-nanofinger device is exposed to a liquid. At 1020 sufficient time is allowed for the liquid to wet the plurality of nanofingers of the metallic-nanofinger device. At 1030 the metallic-nanofinger device is purged of the liquid. At 1040 sufficient time is allowed for at least one nanofinger and a second nanofinger to self-arrange into a close-packed configuration with at least one analyte molecule disposed between at least one metallic cap and a second metallic cap of the respective nanofinger and second nanofinger.

Figure 10B:
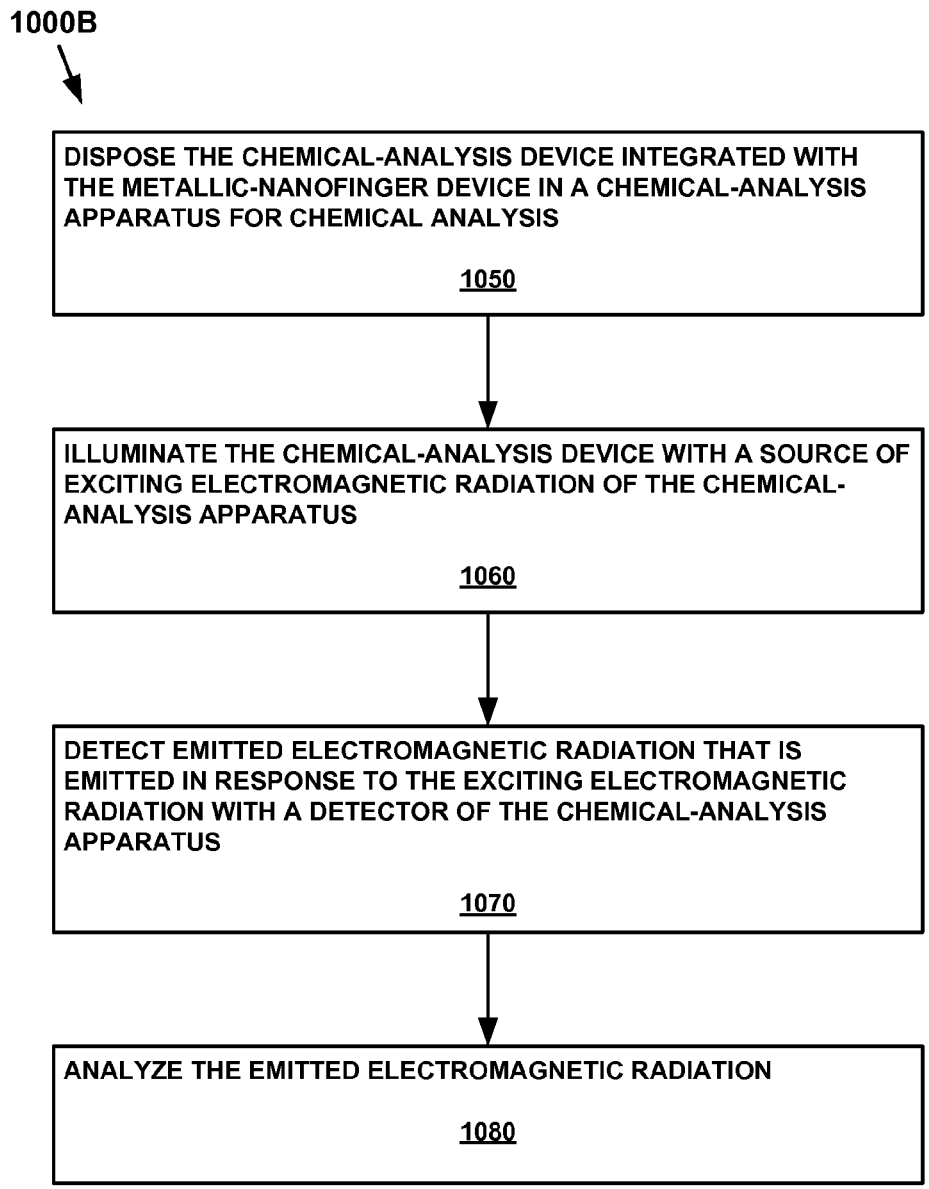
FIG. 10B is a flowchart of further operations that may be employed in the method for using the chemical-analysis device integrated with the metallic-nanofinger device for chemical sensing, in accordance with one or more examples of the present invention.

With reference now to FIG. 10B, in accordance with one or more examples of the present invention, a flowchart 1000B is shown of further operations that may be employed in the method for using a chemical-analysis device integrated with the metallic-nanofinger device for chemical sensing. The method for using the chemical-analysis device integrated with the metallic-nanofinger device for chemical sensing may further include the following operations. At 1050 the chemical-analysis device integrated with the metallic-nanofinger device is disposed in a chemical-analysis apparatus for chemical analysis. At 1060 the chemical-analysis device is illuminated with a source of exciting electromagnetic radiation of the chemical-analysis apparatus. At 1070 emitted electromagnetic radiation is detected that is emitted in response to the exciting electromagnetic radiation with a detector of the chemical-analysis apparatus. At 1080 the emitted electromagnetic radiation is analyzed. Moreover, in another example of the present invention, the method may further include an operation in which operations 1050 through 1080 are performed both before and after performing operations 1010 through 1040.

Examples of the present invention include a metallic-nanofinger device 101 for chemical sensing that can provide enhanced sensitivity for the presence of analyte molecules through surface-enhanced luminescence. Moreover, examples of the present invention provide for lower detectability limits in surface-enhanced luminescence of an analyte associated with an analyte molecule in solution. Examples of the present invention may also be implemented without a spectrometer, or a laser light source. On the other hand, if a Raman spectrometer is used, examples of the present invention also provide for lower detectability limits in SERS analysis of a molecule. Thus, due to the enhanced sensitivity and detectability limits for molecular detection provided by examples of the present invention, the inventors expect new applications of examples of the present invention in at least medical, environmental, chemical, and biological technologies, without limitation thereto.

The foregoing descriptions of specific examples of the present invention have been presented for purposes of illustration and description. They are not intended to be exhaustive or to limit the invention to the precise forms disclosed, and many modifications and variations are possible in light of the above teaching. The examples described herein were chosen and described in order to best explain the principles of the invention and its practical application, to thereby enable others skilled in the art to best utilize the invention and various examples with various modifications as are suited to the particular use contemplated. It may be intended that the scope of the invention be defined by the claims appended hereto and their equivalents.

What is claimed is:

1. A chemical-analysis device integrated with a metallic-nanofinger device for chemical sensing, said chemical-analysis device comprising:
 a metallic-nanofinger device for chemical sensing, said metallic-nanofinger device comprising:
  a substrate; and
  a plurality of nanofingers coupled with said substrate, a nanofinger of said plurality comprising:
   a flexible column; and
   a metallic cap coupled to an apex of said flexible column;
  wherein at least said nanofinger and a second nanofinger of said plurality of nanofingers are to self-arrange into a close-packed configuration with at least one analyte molecule disposed between at least said metallic cap and a second metallic cap of respective nanofinger and second nanofinger; and
  wherein a morphology of said metallic cap is to generate a shifted plasmonic resonance peak associated with amplified luminescence from said analyte molecule; and
 a platform with which said metallic-nanofinger device is coupled.

2. The chemical-analysis device of claim 1, wherein said metallic-nanofinger device is to produce a change in optical response from said metallic-nanofinger device upon exposing said chemical-analysis device to a liquid, and purging said metallic-nanofinger device of said liquid.

3. The chemical-analysis device of claim 1, said chemical-analysis device further comprising:
 an enclosure encapsulating said metallic-nanofinger device and to confine said analyte molecule within said enclosure, said enclosure comprising:
  a micro-fluidic channel to transport a liquid to and from said metallic-nanofinger device disposed within a portion of said micro-fluidic channel.

4. The chemical-analysis device of claim 1, said chemical-analysis device further comprising:
 an enclosure encapsulating said metallic-nanofinger device and to confine said analyte molecule within said enclosure, said enclosure comprising:
  a combined micro-fluidic channel and waveguide configured both to transport a liquid to and from said metallic-nanofinger device contained within a portion of said micro-fluidic channel, and to conduct exciting electromagnetic radiation to said metallic-nanofinger device and emitted electromagnetic radiation away from said metallic-nanofinger device.

5. The chemical-analysis device of claim 1, said chemical-analysis device further comprising:
 an enclosure encapsulating said metallic-nanofinger device and to confine said analyte molecule within said enclosure, said enclosure comprising:
  an enclosure cover;
  an enclosure base;
  enclosure sidewalls attached to said enclosure cover and attached to said enclosure base;
  an enclosure inlet to admit a liquid into said enclosure; and
  an enclosure outlet to remove said liquid from said enclosure.

6. The chemical-analysis device of claim 5, wherein a component of said chemical analysis device, which is selected from the group consisting of said enclosure cover, said enclosure base, said enclosure sidewalls, said platform, said substrate, and a combination thereof, is transparent to exciting electromagnetic radiation and to emitted electromagnetic radiation.

7. The chemical-analysis device of claim 1, wherein said plurality of nanofingers coupled with said substrate of said metallic-nanofinger device further comprises:
 a coating encapsulating said metallic cap; and
 wherein said coating is to develop a response upon exposure to a liquid.

8. The chemical-analysis device of claim 7, further comprising:
 a chemical-sensing chip, comprising:
  said metallic-nanofinger device for chemical sensing, said device further comprising:
   an array of patches, a patch of said array comprising:
    said plurality of nanofingers coupled with said substrate; and
   wherein said coating of said metallic cap in said patch is functionalized with certain probe species to develop a specific response upon exposure to certain targets in said liquid.

9. The chemical-analysis device of claim 8, wherein each patch of said array of patches further comprises:
 a micro-fluidic channel configured both to confine said analyte molecule within said micro-fluidic channel, and to transport said liquid to and from said metallic-nanofinger device disposed within a portion of said micro-fluidic channel; and
 wherein said array of patches is configured as a lab-on-chip.

10. The chemical-analysis device of claim 1, wherein said chemical-analysis device further comprises:
 a test strip.

11. A chemical-analysis apparatus, comprising:
 a chemical-analysis device integrated with a metallic-nanofinger device for chemical sensing, said chemical-analysis device comprising:
  a metallic-nanofinger device for chemical sensing, said metallic-nanofinger device comprising:
   a substrate; and
   a plurality of nanofingers coupled with said substrate, a nanofinger of said plurality comprising:
    a flexible column;
    a metallic cap coupled to an apex of said flexible column; and
    a coating encapsulating said metallic cap;
   wherein at least said nanofinger and a second nanofinger of said plurality of nanofingers are to self-arrange into a close-packed configuration with at least one analyte molecule disposed between at least said metallic cap and a second metallic cap of respective nanofinger and second nanofinger;
   wherein a morphology of said metallic cap is to generate a shifted plasmonic resonance peak associated with amplified luminescence from said analyte molecule; and
  wherein said coating is to develop a response upon exposure to a liquid; and
  a platform with which said metallic-nanofinger device is coupled; and
 a source of exciting electromagnetic radiation to excite said analyte molecule captured by said chemical-analysis device; and
 a detector to detect emitted electromagnetic radiation that may be emitted from said analyte molecule in response to said exciting electromagnetic radiation.

12. The chemical-analysis apparatus of claim 11, further comprising:
an instrument selected from the group consisting of a colorimeter, a reflectometer, a spectrometer, a spectrophotometer, a Raman spectrometer, an optical microscope, and an instrument to accept said chemical-analysis device for optical analysis.

* * * * *